(12) United States Patent
Fuller et al.

(10) Patent No.: US 8,172,861 B2
(45) Date of Patent: May 8, 2012

(54) COMPOSITIONS AND METHODS FOR JOINING NON-CONJOINED LUMENS

(75) Inventors: Gerald G. Fuller, Stanford, CA (US); C. Travis Rappleye, San Jose, CA (US); Evgenia Mandrusov, Santa Clara, CA (US)

(73) Assignee: TauTona Group, L.P., Menlo Park, CA (US)

( * ) Notice: Subject to any disclaimer, the term of this patent is extended or adjusted under 35 U.S.C. 154(b) by 588 days.

(21) Appl. No.: 12/340,586

(22) Filed: Dec. 19, 2008

(65) Prior Publication Data

US 2009/0162438 A1  Jun. 25, 2009

Related U.S. Application Data

(60) Provisional application No. 61/015,660, filed on Dec. 20, 2007.

(51) Int. Cl.
 *A61B 17/08* (2006.01)
 *A61F 13/00* (2006.01)
 *A61K 9/14* (2006.01)

(52) U.S. Cl. .......................... 606/153; 424/422; 424/484

(58) Field of Classification Search .................. 606/214, 606/213, 153, 155; 424/422, 423, 426, 427, 424/428, 484, 486; 514/20.8; 623/1.1
See application file for complete search history.

(56) References Cited

U.S. PATENT DOCUMENTS

| | | | |
|---|---|---|---|
| 3,740,421 A | 6/1973 | Schmolka et al. | |
| 4,188,373 A * | 2/1980 | Krezanoski | 514/20.8 |
| 4,657,019 A | 4/1987 | Walsh et al. | |
| 4,770,176 A | 9/1988 | McGreevy et al. | |
| 5,141,516 A | 8/1992 | Detweiler | |
| 5,143,731 A | 9/1992 | Viegas et al. | |
| 5,180,392 A * | 1/1993 | Skeie et al. | 606/155 |
| 5,183,879 A | 2/1993 | Yuasa et al. | |
| 5,366,735 A | 11/1994 | Henry | |
| 5,525,334 A | 6/1996 | Ito et al. | |
| 5,534,186 A | 7/1996 | Walker et al. | |
| 5,549,122 A * | 8/1996 | Detweilwer | 606/153 |
| 5,565,139 A | 10/1996 | Walker et al. | |
| 5,575,815 A * | 11/1996 | Slepian et al. | 623/1.1 |
| 5,589,568 A | 12/1996 | Higashijima et al. | |
| 5,631,011 A * | 5/1997 | Wadstrom | 424/422 |
| 5,643,246 A | 7/1997 | Leeb et al. | |
| 5,651,979 A | 7/1997 | Ron et al. | |
| 5,653,744 A | 8/1997 | Khouri | |
| 5,681,576 A | 10/1997 | Henry | |

(Continued)

FOREIGN PATENT DOCUMENTS

CN  1377706  11/2002

(Continued)

OTHER PUBLICATIONS

U.S. Appl. No. 12/367,201, filed Feb. 6, 2009, C. Travis Rappleye et al.

(Continued)

*Primary Examiner* — Julian Woo
(74) *Attorney, Agent, or Firm* — Foley & Lardner LLP

(57) ABSTRACT

Sol-gel compositions, methods, and kits for joining together non-conjoined lumens in a patient's body including vascular lumens. More particularly, in various aspects, this invention provides thermoreversible sol-gel compositions, methods, and kits for joining such non-conjoined lumens, including small lumens typically requiring microsurgical technique.

38 Claims, 4 Drawing Sheets

U.S. PATENT DOCUMENTS

| | | | |
|---|---|---|---|
| 5,695,480 A | 12/1997 | Evans et al. | |
| 5,702,361 A | 12/1997 | Evans et al. | |
| 5,702,717 A | 12/1997 | Cha et al. | |
| 5,726,456 A | 3/1998 | Lupton et al. | |
| 5,787,900 A | 8/1998 | Butler et al. | |
| 5,834,007 A | 11/1998 | Kubota | |
| 5,858,746 A | 1/1999 | Hubbell et al. | |
| 5,861,174 A | 1/1999 | Stratton et al. | |
| 6,004,573 A | 12/1999 | Rathi et al. | |
| 6,018,033 A | 1/2000 | Chen et al. | |
| 6,201,065 B1 | 3/2001 | Pathak et al. | |
| 6,309,663 B1 | 10/2001 | Patel et al. | |
| 6,413,537 B1 | 7/2002 | Kwon et al. | |
| 6,488,954 B1 | 12/2002 | Yoon et al. | |
| 6,562,362 B1 | 5/2003 | Bae et al. | |
| 6,660,247 B1 | 12/2003 | Gutowska et al. | |
| 6,743,436 B1 | 6/2004 | Lee et al. | |
| RE38,558 E | 7/2004 | Emanuele et al. | |
| 6,761,824 B2 | 7/2004 | Reeve et al. | |
| 6,761,903 B2 | 7/2004 | Chen et al. | |
| 6,897,064 B2 | 5/2005 | Yoshioka et al. | |
| 6,923,986 B2 | 8/2005 | Pathak et al. | |
| 6,939,364 B1 | 9/2005 | Soltz et al. | |
| 6,977,045 B2 | 12/2005 | Reeve et al. | |
| 6,979,464 B2 * | 12/2005 | Gutowska | 424/484 |
| 6,991,804 B2 | 1/2006 | Helmus et al. | |
| 7,011,677 B2 | 3/2006 | Wallace et al. | |
| 7,018,645 B1 | 3/2006 | Piao et al. | |
| 7,033,571 B2 | 4/2006 | Gutowska et al. | |
| 7,044,982 B2 | 5/2006 | Milbocker | |
| 7,083,806 B2 | 8/2006 | Rippon et al. | |
| 7,160,931 B2 | 1/2007 | Cheng et al. | |
| 7,169,404 B2 | 1/2007 | Hossainy et al. | |
| 7,193,007 B2 | 3/2007 | Cheng et al. | |
| 7,641,643 B2 | 1/2010 | Michael et al. | |
| 2003/0191209 A1 | 10/2003 | Guan et al. | |
| 2004/0220283 A1 | 11/2004 | Zhang et al. | |
| 2004/0253277 A1 | 12/2004 | Meadows et al. | |
| 2004/0266983 A1 | 12/2004 | Reeve et al. | |
| 2005/0008610 A1 | 1/2005 | Schwarz et al. | |
| 2005/0027019 A1 | 2/2005 | Zhang et al. | |
| 2005/0079147 A1 | 4/2005 | Delaey et al. | |
| 2005/0143678 A1 | 6/2005 | Schwarz et al. | |
| 2005/0147585 A1 | 7/2005 | Schwarz et al. | |
| 2005/0181062 A1 | 8/2005 | Appel et al. | |
| 2005/0220881 A1 | 10/2005 | Mehta et al. | |
| 2006/0078616 A1 | 4/2006 | Georgewill et al. | |
| 2006/0269512 A1 | 11/2006 | McDougal et al. | |
| 2007/0202177 A1 | 8/2007 | Hoang | |
| 2007/0237740 A1 | 10/2007 | Reddington et al. | |
| 2008/0031847 A1 | 2/2008 | Cohn | |
| 2008/0045985 A1 | 2/2008 | Gurtner et al. | |
| 2008/0181952 A1 | 7/2008 | Vogel et al. | |
| 2008/0208163 A1 | 8/2008 | Wilkie | |
| 2008/0215036 A1 | 9/2008 | Vogel et al. | |
| 2008/0262519 A1 | 10/2008 | Gurtner et al. | |
| 2009/0187199 A1 | 7/2009 | Gurtner et al. | |

FOREIGN PATENT DOCUMENTS

| | | |
|---|---|---|
| EP | 0 327 325 | 8/1989 |
| EP | 0 386 960 | 9/1990 |
| EP | 1 266 570 | 12/2002 |
| EP | 0 724 888 | 5/2003 |
| EP | 1 407 791 | 4/2004 |
| KR | 20040028336 | 4/2004 |
| WO | WO 96/33673 | 10/1996 |
| WO | WO 2007/149999 | 12/2007 |
| WO | WO 2008/073938 | 6/2008 |
| WO | WO 2009/086206 | 7/2009 |
| WO | WO 2009/086207 | 7/2009 |
| WO | PCT/US2010/023155 | 2/2010 |

OTHER PUBLICATIONS

Bavbek, T. et al., "Problems with Attempted Chorioretinal Venous anastomosis by Laser for Nonischemic CRVO and BRVO", 2005, vol. 219, No. 5, pp. 1-2.

Beltran, S. et al., "Swelling Equilibria for Weakly Ionizable, Temperature-Sensitive Hydrogels", Macromolecules, 1991, vol. 24, No. 2, pp. 549-551.

Chen, G. et al., "Graft Copolymers That Exhibit Temperature-induced Phase Transitions Over a Wide Range of pH", Nature, 1995, vol. 373, pp. 49-52.

Cong, Z et al., "Experimental Study on Microvascular Anastomosis Using a Dissolvable Stent Support in the Lumen", Microsurgery, 1991, vol. 12, pp. 67-71.

Dumortier et al., "A Review of Polexamer 407 Pharmaceutical and Pharmacological Characteristics" Pharmaceutical Research, 2006, vol. 23, No. 12, pp. 2709-2728.

Escobar-Chavez et al., "Applications of Thermo-Reversible Pluronic F-128 Gels in Pharmaceutical Formulations," J. Pharm Pharmaceut. Sci. (www.csps Canada.org), vol. 9, No. 3, pp. 339-358 (2006).

Kamiji, T. et al., "Microvascular anastomosis using polyethylene glycol 4000 and fibrin glue," British Journal of Plastic Surgery, 1989, vol. 42, pp. 54-58.

Kania, N. M. et al., "A new method of microvascular anastomosis: Clips with a soluble stent", 1998, pp. 245-248. (English abstract provided).

Leung, P.C. et al., "Biodegradable, Thermosensitive Implant for Approximating Cylindrical Structures: A Preliminary Study", Microsurgery, 2003, vol. 23, pp. 123-129.

Moskovitz, M., "Microvascular Anastomoses Utilitzing New Intravascular Stents", Annals of Plastic Surgery, 1994, vol. 32, pp. 612-618.

Nakata, S. et al., "End-to-side and end-to-end vascular anastomoses with a carbon dioxide laser", The Journal of Thoracic and Cardiovascular Surgery, 1989, vol. 98, pp. 1-2.

Park, T.G. et al., "Synthesis, Characterization, and Application of pH/Temperature-Sensitive Hydrogels", Proceed. Intern. Symp. Control. Rel. Bioact. Mater, 1990, vol. 17, pp. 112-113.

Park, T.G. et al., "Temperature Modulated Protein Release From pH/Temperature Sensitive Hydrogels" Biomaterials, 1999, vol. 20, pp. 517-521.

Steedman, H.F., "A New Ribboning Embedding Medium for Histology", Nature, 1957, vol. 179, pp. 1345.

Zhang, J. et al., "Synthesis and Characterization of pH-and Temperature-Sensitive Poly(Methacrylic acid)/Poly(N isopropylacrylamide) Interpenetrating Polymeric Networks" Macromolecules, 2000, vol. 33, pp. 102-107.

* cited by examiner

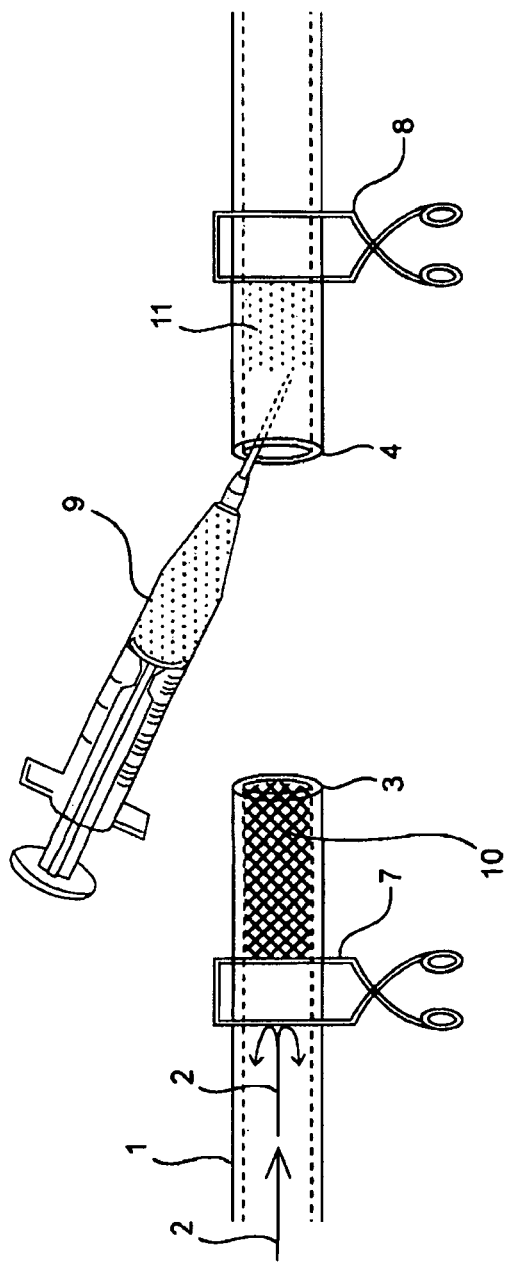
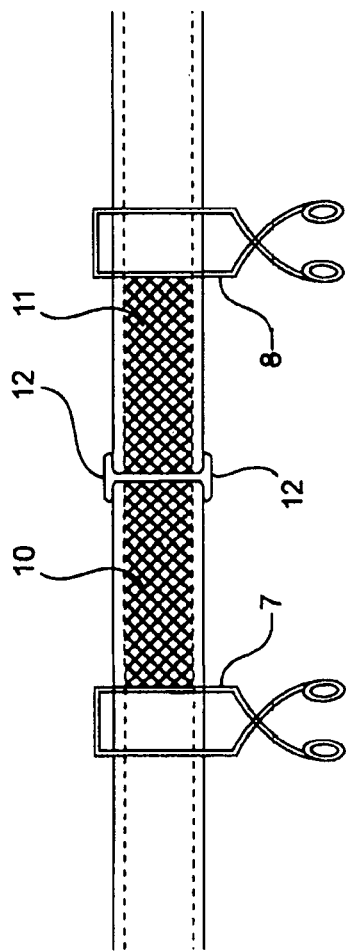

COMPOSITIONS AND METHODS FOR JOINING NON-CONJOINED LUMENS

CROSS-REFERENCE TO RELATED APPLICATIONS

This application claims the benefit under 35 U.S.C. §119(e) of Provisional Patent Application Ser. No. 61/015,660, filed on Dec. 20, 2007, which is incorporated herein by reference in its entirety.

FIELD OF THE INVENTION

This invention relates generally to compositions, methods, and kits for joining together non-conjoined lumens in a patient's body including vascular lumens. More particularly, in various aspects, this invention provides compositions, methods, and kits for joining such non-conjoined lumens, including small lumens typically requiring microsurgical techniques.

BACKGROUND OF THE INVENTION

Non-conjoined lumens arise in a variety of settings including surgical settings where the non-conjoined lumens are intentionally created or arise from lacerations or puncture wounds. Intentionally created non-conjoined lumens include those arising during surgical repair of e.g., treatment of a blockage in a lumen by bypass procedures, attaching a synthetic graft or during free tissue transfer in cosmetic surgical settings. Anastomosis is conducted to surgically reconnect the open ends of the lumen. Examples of anastomosis procedures include anastomotic procedures on the vasculature, the vas deferens, the fallopian tubes, the urinary tract, tear ducts, bowel, mammary glands, alimentary ducts, pancreatic ducts, bile ducts, etc. In each case, the anastomosis procedure creates a channel for the flow of a body fluid there through.

The anastomosis may be, for example, end-to-end, end-to-side, and side-to-side. As is apparent from their names, anastomosis may involve various configurations. For instance, one tubular tissue may be joined end-to-side with two tubular tissues, creating a three-channeled tubular tissue construct.

In the surgical context, end-to-end anastomosis, as is apparent from its name, is a surgical procedure for connecting an end or distal portion of one tubular tissue structure to an end or distal portion of another tubular tissue structure, such that a continuous lumen is created. (As used herein, "end" or "distal portion," refers to the open end of the tubular tissue.)

In an end-to-side anastomosis, a tubular tissue structure having a hole or open part is connected through the open part to an open or distal end of a tubular tissue to form a continuous lumen with a branched configuration. Similarly, in a side-to-side anastomosis, two non-conjoined lumens are merged together into a continuous lumen though a hole or opening on each of the lumens to be joined.

A successful anastomosis typically involves the smooth connection of lumens, such that the internal structure is not blocked and internal body fluid flow—such as blood, semen or food or gastrointestinal fluids—is restored or improved. Ideally, the matching up/ligation surgical procedure is rapid and precise, so that patient exposure while in a vulnerable state—such as having blood flow stopped—is minimized.

There are a variety of tubular tissues, and the lumen of the first tubular tissue may not be of the same diameter as the lumen of the second tubular tissue. Thus, because the delicate surgery may involve matching and ligating two (or more) non-identical tubular tissues, various ligation techniques have been used with varying rates of success. These include sutures, tissue adhesives, adhesive strips, and staples, clips and other devices. To some extent all of these materials involve the skill of the practitioner in anastomosis which is accurate, durable and free from conditions which could cause latent deleterious reactions in vivo.

The labor-intensive needle and thread remains the most-used technology as of the present day. Because of the complexity and judgment required in suturing, automated techniques are not well accepted. Calcified and diseased vessels provide mechanical challenges. Sutures may, in some instances, cause a reaction resulting in long term stenosis or fibrosis.

Other approaches to anastomosis include the use of sealants and bioglues for ligation. These may be used individually or in conjunction with suturing or other mechanical ligation techniques or devices. For example, one commercially available sealant CoSeal® (Angiotech Pharmaceuticals, Inc., Vancouver, B.C., Canada) may complement suturing in cardiovascular surgeries Mechanical anastomosis devices, such as clips, are also available. One commercially available device, the U-Clip™ (Medtronic, Minneapolis, Minn. 55432 USA), essentially provides a sharp, nitinol hook for knotting to compete anastomosis. The nitinol allows reversible deformation. The C-Port® (Cardica, Inc. Redwood City, Calif. 94063 USA) and related products are commercially available and use miniature stainless steel staples to securely attach the bypass graft to the coronary artery.

But, before ligating end-to-end, for example, the practitioner must match up the lumens by the circumference of the vessel, using blood vessels as an illustration. Frequently, this is troublesome to the practitioner because the end of an tubular tissue—such as a clamped blood vessel devoid of blood—is not a perfectly round circle; rather it is in its unpressurized, deflated-looking state where a cross-sectional view of the circumference may be a circle, an oval or irregular, and, of course having no structural support from within, is unstably in any shape (unless the surrounding tissue possesses structural strength). The size of the vessels to be so connected may be different. Although blood vessels, for example, or other tubular tissues are somewhat elastic (deformable and returning to the original shape) or plastic (deforming, and not fully returning to the original shape), connecting the circumferences of the lumens such that upon ligation there is no or minimal leakage (in the vascular context, for example), requires a skilled practitioner.

In a microvascular context, anastomosis is performed between ends of blood vessels in the course of, for example, reattaching severed body parts or transplanting organs or tissue. Microvascular anastomosis is often performed by hand under a microscope, and is tedious and painstaking work. The blood vessels connected together often have different diameters, both of which are very small, on the order of about 1 to about 5 millimeters ("mm"). Although blood vessels are usually at least somewhat elastic, the practitioner must match up end to end (for example) two different-shaped-different-sized circumferences and then stitch them together (for example). As a result, it can take many hours to complete just the microvascular anastomosis required to reconnect a severed body part or transplant an organ.

One attempt to provide a mechanism for performing such a microvascular anastomosis is the Microvascular Anastomotic Coupler System, available from Bio-Vascular, Inc. (San Diego, Calif., USA). In this mechanism, an end of each vessel to be connected is essentially turned outward ("everted") over a ring with a forceps or similar instrument. Each ring includes a number of pins over which the vessel is everted. The rings are then pressed together, such that the pins on each ring enter recesses in the other ring, connecting the rings and holding the ends of the vessels together. This system, however, is limited to use with two blood vessels having substantially the same diameter. Further, manual eversion of a blood vessel having a diameter on the order of one millimeter is difficult and painstaking, particularly when the eversion is to be substantially even around the circumference of the ring. Further, the rings provide a noncompliant anastomosis between the two vessels. Thus, although stabilizing the circumference facilitates the ability of the practitioner to match up vessels for end-to-end microvascular anastomosis, the device requires, essentially, practitioners skilled in microsurgical techniques.

For patients and practitioners, perhaps the most demanding anastomosis is incident to heart revascularization. The arteries that bring blood to the heart muscle (coronary arteries) can become clogged by plaque (a buildup of fat, cholesterol and other substances). This can slow or stop blood flow through the heart's blood vessels, leading to chest pain or a heart attack. Increasing blood flow to the heart muscle can relieve chest pain and reduce the risk of heart attack. A patient may undergo one, two, three or more bypass grafts, depending on how many coronary arteries are blocked.

Coronary artery bypass graft surgery ("CABG", sometimes pronounced "cabbage" by practitioners) reroutes, or "bypasses," blood around clogged arteries to improve blood flow and oxygen to the heart. In performing the CABG anastomosis, a segment of a healthy blood vessel from another part of the body is used to make a detour around the blocked part of the coronary artery. This healthy blood vessel may be, for example, an artery present in the thoracic cavity, or may be a piece of a long vein from the patient's leg. In some circumstances, grafts from non-autologous sources may be used, such as synthetic tubular tissues or animal tubular tissues. Regardless of the source of the healthy blood vessel, one end is connected to the large artery leaving the patient's heart (the aorta), and the other end is attached or "grafted" to the coronary artery below the blocked area. In this way of "rewiring" the vasculature, substantially unobstructed blood flow to the heart muscle is resumed.

Conventionally, a pump oxygenator (heart-lung machine) is used for coronary bypass graft operations. Medicines are used to stop the patient's heart, which allows the practitioner to operate without the heart beating. The heart-lung machine keeps oxygen-rich blood moving throughout the patient's body. For this conventional heart bypass graft surgery, a team of practitioners is needed (a surgeon, cardiac anesthesiologist and surgical nurse, and a perfusionist (blood flow specialist)). Multiple practitioners, additional complexity, and, as a practical matter, additional health care cost is involved over surgical procedures involving fewer practitioners and procedures.

Moreover, blood quality may be degraded as the heart-lung machine repetitively pumps the patient's blood through the systemic circulation. The blood may embolize or clot in the distal circulation, or form clots which migrate to the distal vasculature, and cause a stroke.

Off pump coronary artery bypass surgery may reduce this risk. "Off Pump" coronary artery bypass grafting, also called beating heart bypass grafting, takes place while the heart continues to beat, but a mechanical device may be used in an attempt to steady the surrounding vasculature, so that the practitioner can perform the graft. Frequently, because the graft must be performed on arteries in locations directly affected by the beating heart, stabilizing mechanisms are not thoroughly effective, and the practitioner must suture the graft while the graft is moving in conjunction with the heart beat, at least to some extent. Thus, the graft quality may be compromised.

Although, in a bypass surgery time is of the essence, the practitioner cannot rush through without thoroughly and precisely anastomising the graft(s). In conventional coronary artery bypass surgery, three critical determinates that affect the outcome of a bypass surgery are:

(1) time the patient spends on cardiopulmonary bypass,
(2) time the patient spends with a clamped aorta, and
(3) the quality of the anastomosis.

After an hour, the risk of patient morbidity is thought to increase perhaps due to the heart-lung machine degrading the quality of the blood as it is circulated through the systemic circulation. Bypass surgeries, however, often last three hours or longer. Moreover, where the aorta is clamped and blood therefore cannot pass through, the blocked blood is thought to cause additional issues.

Anastomosis is time-consuming. The average time for suturing one anastomosis is approximately fifteen to sixty minutes. An average CABG procedure is thought to involve approximately five anastomoses. Therefore, the average time for graft suturing exceeds the sixty-minute threshold for increased patient morbidity. Patients treated with conventional coronary surgery and placed on cardiopulmonary bypass would benefit from reducing the amount of time spent performing each anastomosis.

In "off pump" procedures where the heart remains beating, the difficulty of suturing an anastomosis graft on a moving surface of the heart may degrade the quality of such grafts completed on patients. An anastomosis differs from straight line suturing in that each suture has a different orientation that is based on its position around the cross-sectional circumference of the blood vessel graft. It can be appreciated that some of the sutures are easily made from on top of the conduit or blood vessel graft, while others are more difficult to complete as they are beneath the conduit. It can be further appreciated that performing such complex suturing procedures on a moving platform, such as the beating heart, further increases the difficulty associated with such suturing procedures. Improperly connecting blood vessel grafts to the patient may present substantial post-operative complications and/or increase operating room time spent correcting the improperly connected graft.

Accordingly, for surgical anastomosis, both practitioners and patients would benefit from faster procedures allowing patients to minimize procedure time, and simpler methods allowing reduced complexity, ease of use and higher quality anastomosis with fewer complications.

SUMMARY OF THE INVENTION

This invention is directed to the discovery that the stabilization of the geometry of the distal portions of tubular tissues or lumens facilitates joining such non-conjoined lumens.

In one aspect, this invention provides novel thermoreversible sol-gel compositions for surgical use to stabilize the geometry of the terminal portion of a lumen to be joined with another lumen, which compositions have a phase transition temperature from a liquid phase to a gel phase of at least 1° C. above or below the temperature of the surgical field and an elastic modulus of at least 8,000 Pascals. In some embodiments, the compositions comprise at least one poloxamer in an aqueous solvent. In some embodiments, the compositions comprise at least two poloxamers in an aqueous solvent.

In some embodiments, the invention provides a composition which comprises:
   a) about 25 to 33% of a mixture of poloxamer 407 and poloxamer 188 in a ratio of between 3:1 and 0.8:1;
   b) an aqueous salt solution having an ionic strength of 0.05 M to 0.4 M;
   c) a phase transition temperature from a liquid phase to a gel phase of at least 1° C. above or below the temperature of the surgical field; and
   d) an elastic modulus of at least 8,000 Pascals in the gel phase.

In another aspect, this invention provides a method of joining at least two non-conjoined lumens in a patient, which method comprises:
   a) applying a thermoreversible sol-gel composition in at least the distal portion of at least one of the lumens in a manner which imparts structural integrity to said portion of the lumen or lumens, which composition has a phase transition temperature from a liquid phase to a gel phase of at least 1° C. above or below the temperature of the surgical field and an elastic modulus of at least 8,000 Pascals in the gel phase, which composition comprises at least two poloxamers in an aqueous solution;
   b) aligning the lumens;
   c) joining the aligned lumens to form a conduit; and
   d) removing the composition thereby establishing body fluid flow through the conduit.

In one embodiment, the method comprises:
   a) applying in a gel phase a thermoreversible sol-gel composition into at least the distal portion of at least one of the lumens which composition has a phase transition temperature from a liquid phase to a gel phase of at least 1° C. above or below the temperature of the surgical field and an elastic modulus of at least 8,000 Pascals in the gel phase, which composition comprises at least two poloxamers in an aqueous solvent;
   b) aligning the lumens;
   c) joining the aligned lumens to form a conduit; and
   d) removing the composition thereby establishing body fluid flow through the conduit.

In another embodiment, the method comprises:
   a) applying in a solution phase a thermoreversible sol-gel composition into at least the distal portion of at least one of the lumens which composition has a phase transition temperature from a liquid phase to a gel phase of at least 1° C. above or below the temperature of the surgical field and an elastic modulus of at least 8,000 Pascals in the gel phase, which composition comprises at least two poloxamers in an aqueous solvent;
   b) transitioning the sol-gel composition from a liquid phase to its solid phase;
   c) aligning the lumens;
   d) joining the aligned lumens to form a conduit; and
   e) removing the composition thereby establishing body fluid flow through the conduit.

In another aspect, this invention provides methods for imaging the joinder of at least two non-conjoined lumens using the methods of this invention and the visualization of the geometry of the distal portions of the lumens in a patient using a sol-gel composition of this invention.

In another aspect, this invention provides methods for visualizing guidance for the methods of this invention for joining at least two non-conjoined lumens in a patient using a sol-gel composition of this invention.

In another aspect, this invention provides a method for evaluating the effectiveness of the methods of this invention for joining non-conjoined lumens in a patient using a sol-gel composition of this invention.

In another aspect, this invention also includes use of any of the materials or methods as disclosed herein for manufacture of a medicament for joining lumens, particularly in a live patient, as further described herein. Thus, in one embodiment, the present invention provides a biocompatible solid mass for use in joining at least two non-conjoined lumens in a patient in a method which comprises:
   a) placing the a sol-gel composition of this invention in at least the distal portion of at least one of the lumens;
   b) aligning the lumens;
   c) closing the aligned lumens to form a conduit; and
   d) removing the solid mass thereby establishing flow through the conduit.

In still another aspect, this invention provides novel kits useful in the methods described above.

These and other embodiments of this invention are further described in the text below. The methods, compositions and kits of this invention may be used in both human and non-human mammals.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 3 is a schematic cross-sectional view of the tubular tissue of FIG. 1 with one end filled with thermoreversible sol-gel (solid or gel phase) and the other end being filled with the sol-gel (liquid phase) via a syringe.

FIG. 4 is a schematic cross-sectional view of the tubular tissue of FIG. 1 with the ends sealed, the gel (solid phase) in place and the clamps still present.

DETAILED DESCRIPTION OF THE INVENTION

Figure 1:
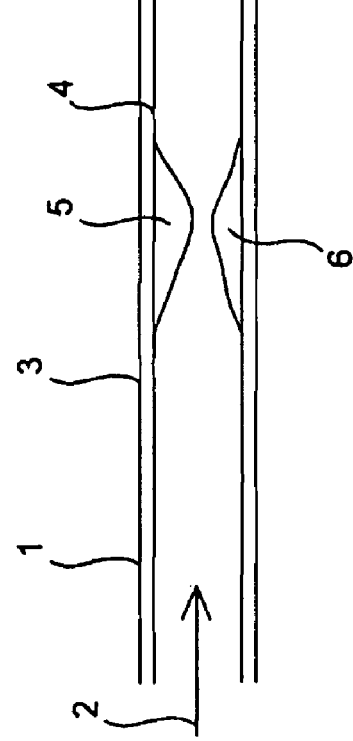
FIG. 1 is a schematic cross-sectional view of a tubular tissue with a partial blockage.

Before the present compositions, medical systems, kits, and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a thermoreversible gel" includes a plurality of such gels and reference to "the adhesive" includes reference to one or more adhesives and equivalents thereof known to those skilled in the art, and so forth.

I. Definitions

Unless defined otherwise, all technical and scientific terms used herein have the same meaning as commonly understood by one of ordinary skill in the art to which this invention belongs. As used herein the following terms have the following meanings. If not defined, a term has its art recognized meaning.

The term "about" when used before a numerical designation, e.g., pH, temperature, amount, concentration, including range, indicates approximations which may vary by (+) or (−) 10%, 5%, 1% or 0.1%.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "patient" refers to mammals and includes humans and non-human mammals.

The term "surgical" relates to any medical procedure where the inner organ or issue of a patient is accessed to investigate and/or treat a pathological condition such as disease or injury, to help improve or alter bodily function or appearance, or for other reasons. As used herein, "surgical" relates to procedures of accessing a patient's inner organ or tissue via an incision or an opening on the patient and via needle-puncture of the skin, such as in percutaneous approaches and other minimally invasive procedures, such as laparoscopic surgeries.

The term "lumen" refers to the hollow tube and the surrounding tissue defining the hollow tube, such as a blood vessel, a vas deferens, a fallopian tube, urinary tract, a tear duct, bowel, a mammary gland, an alimentary duct, a pancreatic duct, a bile duct, and the like. Lumens also includes artificial conduits, such as ePTFE grafts. The term "lumen" is used interchangeably with the term "duct."

The term "conduit" refers to the hollow tube formed by the joined lumens which can accommodate flow of a body fluid after removal of the sol-gel placed therein or clamps placed thereon.

The term "providing" as used in, for example, "providing a sol-gel composition in a distal end of a lumen" and the like, refers to the act of causing a sol-gel composition to be present in the lumen to support the structural integrity of the lumen. The act can be "placing", "delivering" or the like, the sol-gel can be placed in the lumen in a solid state or in a liquid state and being transferred into a solid state while inside the lumen.

The term "non-conjoined lumen" refers to a lumen having an open end or a hole where a body fluid that the lumen carries or should carry will undesirably leak out if the open end or hole is not occluded or connected to another lumen to form a continuous lumen in which the body fluid can circulate or be delivered to the desired destination without undesired leakage.

The term "aligning" refers to the act of bringing the lumens to be joined in a position that the lumens may be connect in a desirable manner, which may include matching up the ends of the lumens and pushing the matched ends of the lumens in contact of each other. Preferably, aligning is done without causing substantial tension to the lumens and to the respective tubular tissues they connect to.

The term "approximating" refers to the act of bringing the lumens to a position or to a close proximity of a position that they are to be connected. When two lumens are approximated, they are close to each other but there may be gaps between the ends of the lumens so that a sol-gel composition can be applied to the inside of the lumens to provide structural support.

The term "biocompatible" as used with terms such as "biocompatible polymer", "biocompatible compound" and the like, refer to materials which, in the amounts employed, are non-toxic and substantially non-immunogenic when used internally in a subject such as a human patient.

The term "thermoreversible sol-gel" refers to a composition, which undergoes a phase transition from a liquid phase to gel phase when the temperature is raised above or reduced below a critical value, which is referred to as "transition temperature." The term "liquid phase" or "liquid state" refers to a liquid or flowable form with a viscosity of less than 2000 Pascal-seconds. The term "gel phase" or "gel state" refers to a gel or relatively solid form with a viscosity of greater than 10,000 Pascal-seconds. As is well known in the science of rheology, complex viscosities of compositions are reported in Pascal-seconds and all viscosities reported in this application are reported as complex viscosities. Such phase transition is reversible. Thus, a thermoreversible sol-gel composition changes from its liquid state to its gel state when the temperature is raised to or above the critical value, or transition temperature, and undergoes a phase transition from the gel state to the liquid state when the temperature is lowered to or below the critical value, or transition temperature. Preferably the phase transition from a liquid to a gel and vice versa occurs in less than 10 minutes, more preferably in less than 5 minutes and even more preferably in less than 2 minute.

For the purpose of this invention, it is desired that the gel has sufficient stiffness or "elastic modulus" to maintain the shape of the filled lumen (i.e. impart structure integrity) during joining of the distal opening of the lumens. The term "gel phase elastic modulus" refers to the stiffness of the sol-gel composition when it is in its gel state or at a temperature above the transition temperature. The term "liquid phase elastic modulus" refers to the stiffness of the sol-gel composition when it is in its liquid state or at a temperature below the transition temperature.

In one embodiment, the thermoreversible sol-gel composition has a modulus of from about 8,000 to 50,000 or 10,000 to 50,000 Pascals and, more preferably, from about 12,000 to 40,000 Pascals.

The term "aqueous solvent" refers to water or a water based solution, e.g. an aqueous salt solution, such as a saline solution, phosphate buffered saline, and other aqueous solutions suitable for dissolving the poloxamers described herein. An aqueous salt solution may contain one or more biocompatible salts selected from sodium chloride (NaCl), potassium chloride (KCl), sodium sulfate ($Na_2SO_4$), sodium bisulfate ($NaHSO_4$), sodium phosphate ($Na_3PO_4$), monosodium phosphate ($NaH_2PO_4$), disodium phosphate ($Na_2HPO_4$), potassium phosphate ($K_3PO_4$), monopotassium phosphate ($KH_2PO_4$), dipotassium phosphate ($K_2HPO_4$), various soluble calcium and magnesium salts, such as calcium chloride ($CaCl_2$), magnesium chloride ($MgCl_2$) and other salts formed by a combination of a cation selected from the group consisting of sodium, potassium, calcium, magnesium, ammonium, and tetraalkylammonium, with an anion selected from the group consisting of chloride, bromide, tartrate, mesylate, acetate, maleate, and oxalate and other biocompatible, water soluble salts including those described in P. Heinrich Stahl, Camille G. Wermuth (Eds.), Handbook of Pharmaceutical Salts Properties, Selection, and Use; 2002.

The term "phosphate buffered saline" or "PBS" refers to a buffer solution which help to maintain a physiological pH and a physiological ionic strength (i.e. isotonic). The final salt concentration of PBS is approximately 137 mM sodium chloride (NaCl), 10 mM phosphate, 2.7 mM potassium chloride, with a pH of 7.4. It may be prepared by diluting a stock solution ten times, which stock solution is prepared by dissolving 800 g sodium chloride (KCl), 20 g potassium chloride, 144 g disodium phosphate ($Na_2HPO_4$) and 24 g monopotassium phosphate ($KH_2PO_4$) in 8 L of distilled water, and topping up to 10 L. PBS can have additional ions such as Calcium ($Ca^{2+}$) or Magnesium ($Mg^{2+}$).

The term "the temperature of the surgical field" refers to temperature of the site where the surgical procedure of joining the non-conjoined lumens is performed. In some embodiments, the temperature of the surgical field refers to the temperature of the vessel wall. Typically, the temperature of the surgical field is close to the body temperature of the patient, but may be somewhat lower than the body temperature of the patient. The difference between the temperature of the surgical field and the patient's body temperature can be affected by a number of factors, such as the size of the incision made in the patient's body, the duration of the exposure, the temperature of the operation room, etc.

The term "distal end" and "opening" of a lumen are used interchangeably herein and refer to the opening of the lumen, for example, the two ends created when a lumen is surgically divided into two parts. "Distal end" or "opening" also refers to a hole cut on part of the wall of a lumen although the lumen is not completely divided, as in the case of an end-to-side or side-to-side anastomosis.

The term "distal portion of the lumen" refers to the portion of the lumen adjacent to the opening in the lumen. Thus, for example, when a lumen is surgically cut, the resulting two openings define the distal portion of what are now first and second lumens. Distal portion of the lumen also refers to the portion adjacent to the hole of a lumen to be used in an end-to-side or side-to-side anastomosis procedure.

The term "joining" refers to any method wherein the first and second lumens are structurally joined together including by way of example, suturing, use of biocompatible glues, lasers, etc. In a preferred embodiment, joining of the lumens is conducted under conditions where there is little or no leakage of body fluid from the juncture of the joined lumens.

The term "substantial completion" as used in, for example, "confirming substantial completion of phase change," refers to the amount of the phase change that would ensure that the sol-gel composition can be safely removed from the anastomosis site by the flow of body fluid in the lumen without causing undesirable blockage in the lumen, for example in a portion of a blood vessel connected to and is smaller than the vessel being joined. In some embodiments, "substantial completion" refers to equal to or greater than about 50%, 80%, 90%, or 95% and up to 100% phase change.

The term "removing the thermoreversible sol-gel composition" refers to removing the sol-gel composition from the conduit formed by the joined lumens. This can be done by transitioning the thermoreversible sol-gel composition from the gel phase to a liquid phase by lowering the temperature to below its transition temperature or by dissolution followed by flushing with the body fluid inside the lumen. Further, any complementary methods of turning the thermoreversible sol-gel composition into a liquid flowable form can also be employed. For example, certain thermoreversible sol-gel compositions can undergo phase transition from a gel to a liquid when triggered by a change in ionic strength, light, pH, etc, alone or in combination with a temperature change. Two or more methods can be combined to facilitate removal of the composition. After the thermoreversible sol-gel composition is removed from the conduit, it will be engrained in the body fluid and become part of the systemic flow of that fluid until removed or cleared by the body.

A "therapeutically active moiety" will be a biologically active moiety. A therapeutic effect is one which seeks to treat the source or symptom of a disease or physical disorder. The term "treat" or "treatment" as used herein refers to: (i) preventing a disease or disorder from occurring in a subject which may be predisposed to the disease or condition but has not yet been diagnosed as having it; (ii) inhibiting the disease or disorder, i.e., arresting its development; and/or (iii) ameliorating or relieving the disease or disorder, i.e., causing regression of the disease. A therapeutically effective amount is sufficient to establish causation of a therapeutic effect, as determined by relevant clinical standards. The therapeutically effective amount will vary depending upon the specific agent incorporated, the subject and disease condition being treated, the weight and age of the subject, the severity of the disease condition, the dosing regimen to be followed, timing of administration, the manner of administration and the like, all of which can be determined readily by one of ordinary skill in the art.

The term "arresting" the flow of a body fluid refers the act of stopping, substantially stopping, or reducing the flow of the body fluid. This can be done a number of ways, such as by using a clamp, providing a vessel loop, silk tie, applying a direct pressure (for example, using a finger or tournequette).

The term "clamp" refers to conventional mechanical devices suitable for application to a lumen to arrest the flow of body fluid therein, for example, stopping or reducing the flow of blood in a vessel, where the devices can be retrieved after they are no longer needed, thereby restoring flow. Clamps include any surgical clamps suitable for clamping the vessels to be operated on from the outside, such as clamps, clips and tourniquets or snares. Clamps also include devices that are applied to the inside of a lumen, such as a balloon catheter that is placed inside a blood vessel and inflated to stop blood flow. Suitable clamps are known in the art.

The terms "adhesive", "surgical adhesive", "glue", "biocompatible glue" or "sealant" and the like are used interchangeably herein. These terms are used to describe compounds which are or can be used in binding one tissue to another tissue. The glue may operate by the formation of covalent bonds and allow the tissues to contact each other and naturally heal or grow together. The adhesive may be comprised of a cyanoacrylate-based adhesive, a fibrin-based adhesive, a polyurethane-based adhesive, a polyisocyanate-based adhesive a polyethylene glycol-based glue, a latex glue, a biologics glue (also known as a protein-based glue, such as those comprising serum albumin (such as human, bovine, or porcine serum albumin), and glutaraldehyde), or an ultraviolet curable glue. The adhesives may include any biocompatible material which when added to the adhesive, produces an open cell geometry upon curing in situ to promote tissue ingrowth. For example, such material can include a foaming agent or porogen, such as sodium chloride, crystals of saccharose, gelatin spheres or paraffin spheres, or an emulsified liquid that is compatible but is immiscible with the glue and can be absorbed by the tissue relatively quickly to leave pores in the glue. Other suitable biocompatible agents are known in the art. It is contemplated that the tissue can infiltrate the glue matrix and heal across as the glue is being reabsorbed by the body. Adhesive materials may be found within publications known to those skilled in the art and reference made to U.S. Pat. No. 7,044,982 issued May 16, 2006 and U.S. Pat. No. 6,939,364 issued Sep. 6, 2005. Both of which are incorporated herein by reference along with the publications cited therein to disclose and describe surgical adhesives to the extent that these disclosures do not contradict the present disclosure. Examples of glues also include, but are not limited to, ArterX® (by Tenaxis Medical, Inc., Mountain View, Calif.), CovaBond® (by Covalent Medical, Inc., Ann Arbor, Mich.), ProGEL VS™ (Neomend, Irvine, Calif.), PPCA & DermaFlex® (by Chemence Medical, Alpharetta, Ga.), Bioglue® (known to be a mixture of bolvine serum albumin and gluderaldehyde, by Cryolife, Inc., Kennesaw, Ga.), Coseal® (by Baxter, Deerfield, Ill.), Microval® (by Medico Corp., Bucuresti, Romania), Omnex® (by Ethicon Inc., Somerville, N.J.), HistoAcryl Blue® (by Aesculap subsidiary of B Braun, in partnership with TissueSeal), Indermil® (by Syneture. Mansfield, Mass.). LiquiBand® (by Advanced Medical Solutions Group, UK), Glubran® (by Gem s.r.l, Italy), GluSeal® (by GluStitch, Canada), Neuroacryl® and TruFill® (by Cordis, Warren, N.J.), and the like. Glues may also include Tissucol® and Tisseel® (by Baxter, Deerfield, Ill.), Avitene® (by Davol, Inc. Providence, R.I.), DuraSeal® (by Confluent Surgical, Waltham, Mass.), Dermabond®, Evicel® and Quixil® (by Ethicon Inc., Somerville, N.J.), LTG® (by MediGlue, Russia), Epiglu® (by Meyer-Haake GmbH Medical Innovations, Germany), TachoSil® (by Nycomed, Austria) and TissuGlue® (by Cohera Medical, Inc., Pittsburgh, Pa.).

II. Compositions

Figure 2:
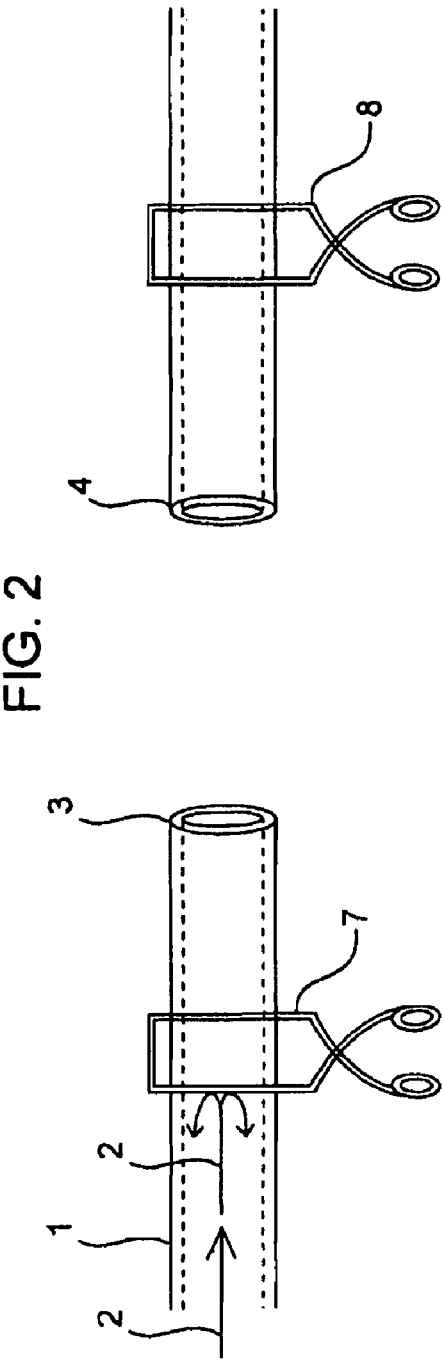
FIG. 2 is a schematic cross-sectional view of the tubular tissue of FIG. 1 wherein the area having the partial blockage has been removed creating two non-conjoined lumens having both ends of the tubular tissue clamped off.

In one aspect, this invention provides a thermoreversible sol-gel composition having unique properties for use in the methods of this invention for joining two or more non-conjoined lumens, for example blood vessels, in a patient. In an illustrative embodiment of the method (a detailed description of the methods of this invention can be found in section "III. Anastomosis Methods" below), two clamps are placed on the vessels to stop blood flow in the section between the clamps prior to severing the vessel, as shown by FIG. 2 (which illustrates the vessel after it has been severed). Thus, it is understandable that due to the outside pressure from the clamps and from manipulations by a surgeon during the anastomosis, coupled with lack of inside pressure in the absence of blood flow, the severed vessels are unlikely to maintain their structural integrity, which will cause difficulties in joining the vessels. Thus, this invention provides a thermoreversible sol-gel composition that can be conveniently placed in the lumens distal to the clamping to provide structural support to the vessels during the joining procedure and can be easily removed after the lumens are joined.

In order to provide sufficient structural support, it is contemplated that the gel state of the sol-gel composition needs to have a minimum stiffness or elastic modulus of at least 8,000 Pascals, 10,000 Pascals, or 12,000 Pascals. In addition, in order to be used safely in a patient, the composition is preferably biocompatible, sterile and stable and have a transition temperature that is within the range tolerable by human tissues. It is preferred that the thermoreversible sol-gel composition has a pH and ionic strength similar to physiological conditions in order to avoid damage to surrounding tissues.

It is contemplated that a transition temperature of at least 1° C. above or below the ambient temperature of the surgical field is used. However, the transition temperature should not exceed 45° C. or be lower than 0° C. in order to be safe to a patient. In some embodiment, the composition has a transition temperature of at least 1° C. above or below the ambient temperature of the surgical field so that it can readily undergo a thermal sol-gel transition under the surgical setting, which may be important to minimize the duration and improve the quality of the procedure. In some embodiment, the composition has a transition temperature of at least 3° C. above or below the ambient temperature of the surgical field.

In some embodiments, the thermoreversible sol-gel composition has a transition temperature of between 33° C. to 38° C., or between 35° C. to 37° C. In some embodiment, the transition temperature is about 35° C. Such a sol-gel composition is a liquid when stored at room temperature and can be delivered to the lumen as a liquid. The composition can then be slightly warmed by a heat source to above the transition temperature to form a gel having a desired stiffness. After the vessels are joined, the heat source can be removed to reduce the temperature to or below the ambient temperature of the surgical field, inducing the gel to change to its liquid state, which upon restoration of blood flow can be diluted and removed from the joined vessel. Compositions with a transition temperature that is lower than the ambient temperature of the surgical field can be delivered as a gel and removed by lowering the temperature to a degree that is lower than the transition temperature but is still within the range the lumen tissue can tolerate. In order to be easily removed from the joined vessel after the anastomosis procedure, it is contemplated that the thermoreversible sol-gel composition should have good aqueous solubility and a liquid phase elastic modulus of no more than 10,000 Pascals so that it can be readily removed and not cause obstruction to the flow of body fluid, such as blood.

In one embodiment, this invention provides a thermoreversible sol-gel composition for providing structural support for a lumen to be joined with another lumen during a surgical operation in a patient that satisfies the above desired parameters. In one embodiment, the sol-gel composition of this invention has a phase transition temperature from a liquid phase to a gel phase of at least 1° C. above or below the ambient temperature of the surgical field and a gel phase elastic modulus of at least 8,000 Pascals, 10,000 Pascals, or 12,000 Pascals at a temperature above the transition temperature. In one embodiment, the transition temperature of the thermoreversible sol-gel composition is at least 3° C. above the ambient temperature of the surgical field. In one embodiment, the composition comprises at least one poloxamer in an aqueous solvent. The aqueous solvent may be water or a biocompatible aqueous salt solution. In one embodiment, the composition comprises at least two poloxamers in an aqueous solvent. In another embodiment, the sol-gel composition has a maximum liquid phase elastic modulus of 10,000 Pascals.

In one embodiment, the thermoreversible sol-gel composition has a transition temperature of between 35° C. and 38° C. In one embodiment, the composition is a liquid having a maximum elastic modulus of 10,000 Pascals at 34° C. and is a gel having a minimum elastic modulus of 12,000 Pascals at 37° C. In one embodiment, the composition has an elastic modulus of at least 17,000 Pascals at 40° C.

In one embodiment, the composition is sterile.

In one embodiment, the pH of the composition is 5-9. In another embodiment, the pH of the composition is 6-8.

It is a result of this invention that a mixture of poloxamer 188 and poloxamer 407, given the right concentration and ratio, generates thermoreversible sol-gel compositions having the above desired properties. Poloxamers are biocompatible polyoxyethylene-polyoxypropylene block copolymers represented by the formula of $HO(C_2H_4O)_a(C_3H_6O)_b(C_2H_4O)_aH$ that are also known by their tradenames such as Pluronics® and Lutrol®. There are several types of poloxamers based on the values of a and b in the formula and their molecular weight, for example, poloxamers 124, 182, 188, 237, 338 and 407. When dissolved in water or an aqueous solvent, they form thermoreversible sol-gel compositions. However, certain mixtures of poloxamer 188 and poloxamer 407 are found to be of particular use in the method of this invention. Poloxamer 188, which is also known as Pluronic® F68 or Lutrol® F68, has an average molecular weight of about 8,400. Poloxamer 407, which is also known as Pluronic® F127 or Lutrol® F127, has an average molecular weight of about 12,5000. It is to be understood that a polymer may contain mixtures of varying molecular weights incidental to the polymerization process.

It is discovered that both the ratio of poloxamer 188 and poloxamer 407 and the total poloxamer concentration affect the properties of the resulting thermoreversible sol-gel composition. At the high limit of the total poloxamer concentration, solubility is a concern. The solubility limit of the total concentration of poloxamers 188 and 407 is about 35%. If the total poloxamer concentration is too low, however, the composition will not be sufficiently stiff when solidifies. At a given ratio of poloxamer 188 and poloxamer 407, an increase in total poloxamer concentration causes an increase in elastic modulus but a decrease in liquid-solid transition temperature. A very low transition temperature may cause problems in delivery and removal of the thermoreversible sol-gel composition because the composition may stay in its gel state at the ambient temperatures of the surgical field, and thus may require cooling to change to its liquid state before it is removed, complicating the anastomosis procedure.

At a given total poloxamer concentration, the transition temperature can be increased by increasing the proportion of the lower molecular weight poloxamer, i.e. poloxamer 188. If the composition is rich in poloxamer 188, the transition temperature will be too high and in order to induce a liquid to gel transition, the temperature of the lumen may have to be raised to a temperature that may cause tissue damage, making it unsafe for its intended purpose. If the composition is rich in poloxamer 407, the transition temperature will be too low. Generally, if two thermoreversible sol-gel compositions have the same transition temperature, the composition with a higher total poloxamer concentration will have a higher gel phase elastic modulus. Thus, to increase the elastic modulus but maintain a desired transition temperature, one need to increase the total concentration of poloxamer and the proportion of poloxamer 188 simultaneously, and vice versa.

Table 1 provides several working examples of the thermoreversible sol-gel composition of this invention as well as examples that do not possess the desired properties for use in the methods of this invention. As shown in Table 1, Formulations 1-3, possess the desired transition temperature and stiffness for use in the methods of this invention. A constant transition temperature can be obtained through increasing the total poloxamer concentration and the poloxamer 188 ratio simultaneously. The stiffness increases with an increase in total poloxamer concentration. However, unbalanced alterations may lead to compositions unsatisfactory the methods. For example, a 28% total concentration combined with a ratio of poloxamer 407 to 188 of 1.55:1 (Formulation 1) gives the desired transition temperature and stiffness. However, increasing the ratio of poloxamer 407 to 2.85:1 (Formulation 5) makes the transition temperature too low so that at 34° C. the composition is still a gel. On the other hand, decreasing the ratio of poloxamer 407 to 1:1 (Formulation 4) makes the transition temperature too high so that at 40° C., the composition is still a liquid. However, a ratio of poloxamer 407 to 188 of 1:1 is operational if the total poloxamer concentration is increased from 28% to 31%.

TABLE 1

| Formulation | Total Conc. | 407:188 Ratio | Transition temperature (° C.) | Modulus at 40° C. (kPa) | Modulus at 37° C. (kPa) | Modulus at 34° C. (kPa) |
|---|---|---|---|---|---|---|
| 1 | 28% | 1.55:1 | 35 | 17.6 | 13.9 | 4.4 |
| 2 | 31% | 1:1 | 35 | 23.5 | 17.1 | 6.2 |
| 3 | 33% | 0.8:1 | 35 | 39.7 | 28.8 | 2.6 |
| 4 | 28% | 1:1 | >40 | 0.5 | 0.4 | 0.3 |
| 5 | 28% | 2.85:1 | <33 | 19.8 | 17.5 | 15 |
| 6 | 33% | 0.67:1 | >40 | 0.008 | 0.001 | 0.0003 |

Thus, in one embodiment, the thermoreversible sol-gel composition of the invention comprises:
 a) about 25 to 33% of a mixture of poloxamer 407 and poloxamer 188 in a ratio of between 3:1 and 0.8:1;
 b) an aqueous salt solution having an ionic strength of 0.05 M to 0.4 M;
 c) a phase transition temperature from a liquid phase to a gel phase of at least 3° C. above or below the temperature of the surgical field; and
 d) an elastic modulus of at least 12,000 Pascals in the gel phase.

In one embodiment, the composition comprises about 25 to 29% of a mixture of poloxamer 407 and poloxamer 188 in a ratio of between 3:1 and 0.8:1.

In one embodiment, the composition comprises about 27 to 29% of a mixture of poloxamer 407 and poloxamer 188 in a ratio of between 1.5:1 and 1.6:1, or between 1.53:1 to 1.57:1.

In one embodiment, the composition comprises about 28% of a mixture of poloxamer 407 and poloxamer 188 in a ratio of about 1.55:1.

In one embodiment, the salt is selected from the group consisting of sodium chloride (NaCl), potassium chloride (KCl), sodium sulfate ($Na_2SO_4$), sodium bisulfate ($NaHSO_4$), sodium phosphate ($Na_3PO_4$), monosodium phosphate ($NaH_2PO_4$), disodium phosphate ($Na_2HPO_4$), potassium phosphate ($K_3PO_4$), monopotassium phosphate ($KH_2PO_4$), dipotassium phosphate ($K_2HPO_4$), various soluble calcium and magnesium salts, such as calcium chloride ($CaCl_2$), magnesium chloride ($MgCl_2$). Other salts include a combination of a cation selected from the group consisting of sodium, potassium, calcium, magnesium, ammonium, and tetraalkylammonium, with an anion selected from the group consisting of chloride, bromide, tartrate, mesylate, acetate, maleate, and oxalate and other biocompatible, water soluble salts include those described in P. Heinrich Stahl, Camille G. Wermuth (Eds.), Handbook of Pharmaceutical Salts Properties, Selection, and Use; 2002. A combination of any two or more salts can be used.

In one embodiment, the aqueous salt solution has an ionic strength that is equal to the ionic strength of a solution having a pH of about 7.4 and comprising a salt concentration of between 68 mM of sodium chloride, 1.3 mM of potassium chloride and 5 mM of phosphate ion to 274 mM of sodium chloride, 5.4 mM of potassium chloride, and 20 mM of phosphate ion.

In one embodiment, the aqueous salt solution is phosphate buffered saline.

In one embodiment, the thermoreversible sol-gel composition comprises:
- about 17% w/w of poloxamer 407;
- about 11% w/w of poloxamer 188;
- and about 72% of phosphate buffered saline solution.

The compositions of this invention are substantially free from polyethylene oxide and polyvinylpyrrolidone.

The thermoreversible sol-gel compositions of this invention may include one or more additional moieties. For example, the composition may contain a biologically active moiety, preferably in a therapeutically effective amount. Examples of such biologically active moiety include anti-thrombotic agents, such as anti-coagulants (for example heparin), platelet inhibitors, and thrombolytic agents; anti-anginals, such as beta-blockers, calcium channel blockers, and nitrates; wound healing agents; growth factors, gene vectors containing growth factors, such as fibroblast growth factor (FGF), insulin-like growth factor (IGF), vascular endothelial growth factor (VEGF), B-cell growth factor (bGF), hepatocyte growth factor (HGF), monocyte chemotactic protein-1 (MCP1), and those described in U.S. Pat. No. 6,702,744, which is incorportated by reference in its entirety, in protein or gene form, or combinations thereof, which may be in sustained release formulations; hormones such as growth hormones, estradiol and other steroids, including corticosteroids; pro-angiogenic agents; anti-vessel spasm agents, such as nitroglycerine; anti-restenosis (anti-proliferative) agents, e.g., the "limus" family drugs such as everolimus, sirolimus, paclitaxel, rapamycin, biolimus (Biosensors International, Singapore), etc.

In some embodiments, the thermoreversible sol-gel compositions of this invention are substantially free of anti-infectives, such as antibiotics, antibacterial, antiviral and antifungal agents; antimicrobials; anti-inflammatory agents, such as diclofenac; and anti-glaucoma agents.

The compositions may also include a contrasting agent. Contrasting agents, such as a biocompatible radio opaque material capable of being monitored by, for example, radiography, may also be added to the sol-gel composition to track and monitor the sol-gel and/or the procedure. The contrasting agent may be water soluble or water insoluble and preferably does not contain radioactivity above the native or endogenous amounts naturally occurring in the elements employed.

Examples of water soluble contrasting agents include metrizamide, iopamidol, iothalamate sodium, iodomide sodium, and meglumine. Examples of water insoluble contrasting agents include tantalum, tantalum oxide, and barium sulfate, each of which is commercially available in the proper form for in vivo use including a preferred particle size of about 10 microns or less. Other water insoluble contrasting agents include gold, tungsten, and platinum powders.

The compositions may also include a suitable biocompatible dye for visualization, especially when a lumen has a thick wall. Such dyes are well known in the art.

III. Anastomosis Methods

In another aspect, this invention provides methods of using a thermoreversible sol-gel composition of this invention to join two non-conjoined lumens in a patient, which methods comprise:
a) applying a thermoreversible sol-gel composition of this invention (as described above) in at least the distal portion of at least one of the lumens in a manner which imparts structural integrity to said portion of the lumen or lumens;
b) aligning the lumens;
c) joining the aligned lumens to form a conduit; and
d) removing the composition thereby establishing body fluid flow through the conduit.

It is contemplated that the present invention can be applied to any anastomotic procedure that connects one hollow tissue structure (lumen) to another hollow tissue structure (lumen), such that the spaces within each hollow tissue structure are connected thereby forming a conduit (an intraluminal conduit). It can be used in a microvascular context, which is performed between ends of blood vessels in the course of, for example, reattaching severed body part and/or transplanting organ or tissue. It can also be used in minimally invasive procedures or percutanteous approaches with catheters. The methods of the invention can be used to connect non-conjoined lumens arising from surgical procedures wherein the originally intact lumen has been severed for the purposes of, e.g., removing a blockage or partial blockage. Suitable lumens include, by way of example, the vasculature, the vas deferens, the fallopian tubes, the urinary tract, tear ducts, bowel, mammary glands, alimentary ducts, pancreatic ducts, bile ducts, etc. (Specific anatomical lumens may be referenced by their conventional anatomical nomenclature such as tubes, ducts or vessels, as used in context herein.)

In one embodiment, a method of this invention comprises:
a) applying in a gel phase a thermoreversible sol-gel composition of this invention (which is described above in details) into at least the distal portion of at least one of the lumens;
b) aligning the lumens;
c) joining the aligned lumens to form a conduit; and
d) removing the composition thereby establishing body fluid flow through the conduit.

In another embodiment, the method comprises:
a) applying in a solution phase a thermoreversible sol-gel composition of this invention (which composition is described in details above) into at least the distal portion of at least one of the lumens;
b) transitioning the sol-gel composition from a liquid phase to a solid phase;
c) aligning the lumens;
d) joining the aligned lumens to form a conduit; and
e) removing the composition thereby establishing body fluid flow through the conduit.

In some embodiments, the method is a method for joining at least two non-conjoined lumens in a patient, wherein at least one of the lumens has a clamp to arrest the flow of the fluid therein, which method comprises:
(a) providing a biocompatible phase-reversible sol-gel composition of this invention in a gel phase in at least the distal portion of at least the lumen having the clamp;
(b) aligning the lumens;
(c) closing the aligned lumens to form a conduit;
(d) inducing a phase transition of the sol-gel wherein the sol-gel changes from the gel phase to a liquid phase;
(e) confirming substantial completion of the phase transition; and
(f) removing the clamp(s) thereby establishing flow through the conduit and removing the sol-gel composition.

In some embodiments, all non-conjoined lumens have clamps.

In some embodiments, the method is a method for joining at least two non-conjoined lumens in a patient, which method comprises:
(a) approximating the lumens in a connecting position;
(b) providing a biocompatible phase-reversible sol-gel composition of this invention in a gel phase in the distal portion of both lumens;
(c) closing the lumens to form a conduit;
(d) inducing a phase transition of the sol-gel wherein the sol-gel changes from the gel phase to a liquid phase; and
(e) establishing flow through the conduit.

In some embodiments of the above method, step (e) comprises (e1) and (e2), wherein (e1) comprises confirming substantial completion of the phase transition, and wherein (e2) comprises removing the clamps thereby establishing flow through the conduit and removing the sol-gel composition.

In some embodiments, the approximating the lumens in a connecting position comprises partially suturing the lumens.

In some embodiments, the above method further comprises a step before the step of providing the sol-gel composition in the lumen, which step comprises arresting the flow of body fluid in the lumens.

In some embodiments, the arresting the flow of body fluid in the lumen comprises clamping at least one of the lumens. In some embodiments, the arresting the flow of body fluid in the lumen comprises clamping all the lumens to be joined.

In some embodiments, the arresting the flow of body fluid in the lumens comprises applying a pressure on at least one of the lumens.

In some embodiments, the method further comprises flushing the distal portion of the clamped lumen with a biocompatible liquid prior to the step of providing the sol-gel composition in the lumen.

In some embodiments, the invention provides a method for joining at least two non-conjoined lumens in a patient, wherein at least one of the lumens has a clamp to arrest the flow of the fluid therein, which method comprises:
flushing the distal portion of the clamped lumen with a biocompatible liquid;
approximating the lumens in a connecting position, which approximating comprises partially suturing the lumens;
providing a biocompatible phase-reversible sol-gel composition of this invention in a gel phase in the distal portion of both lumens;
closing the lumens to form a conduit with a biocompatible adhesive;
inducing a phase transition of the sol-gel wherein the sol-gel changes from the gel phase to a liquid phase;
confirming substantial completion of the phase transition; and
removing the clamps thereby establishing flow through the conduit and removing the sol-gel composition.

In one embodiment used for illustrative purposes only, the anastomosis is performed during coronary artery bypass graft (CABG) procedures or peripheral bypass procedures to connect two blood vessels or one blood vessel with one synthetic graft. The blood vessels connected together may have different diameters. Further one or both of the vessels may be very small, and may be on the order of about 1 to 5 millimeters ("mm"). The microvascular anastomosis procedure using the present invention may be performed under a microscope.

Referring now to the Figures, the invention is described schematically and in a simplistic fashion in order to convey the general concepts. With these concepts in mind those skilled in the art will contemplate detailed specific embodiments of the invention which are intended to be encompassed by the present claims. FIG. 1 shows a schematic cross-sectional view of a lumen which may be a vessel 1 which has flow 2 running there through. A portion of the vessel indicated by points 3 and 4 has a restricted flow due to the formation of blockages 5 and 6. The blockage may become so severe that the flow is completely blocked. Those skilled in the art will appreciate that a range of different treatments are available for restoring flow.

Prior to the operation to restore flow, the vessel needs to be occluded to stop or reduce the fluid (e.g., blood) flow. Such occlusion is important for anastomosis involving a blood vessel to prevent excessive loss of blood and complications caused by a continuous blood flow. This can be achieved by applying at least one clamp on the blood vessel to be operated on or by conventional means, such as applying external pressure, e.g., pressing down with a finger or tournequette, on the vasculature, or providing a vessel loop or vessel tie upstream from the point of severance or on both sides of the point of severance on the blood vessel. However, clamping may not be necessary for anastomosis of other types of lumens where there is no continuous flow of fluid or the amount of fluid does not complicate the procedure.

As shown in FIG. 2, clamps 7 and 8 have been placed on the vessels to stop the blood flow in the section between the clamps prior to removal of the blocked section. Such clamps can be any surgical clamps suitable for clamping the vessels to be operated on from the outside, such as clamps, clips and tourniquets or snares. After clamping, a portion of the vessel 1 which has the restricted flow between the points 3 and 4 is then surgically removed. Those skilled in the art will understand that the distance between the points 3 and 4 is sufficiently small such that the ends can be brought into contact with each other to restore flow.

In some embodiments, after the vessel is cut into two non-conjoined vessels with open ends or after the diseased portion is severed, or in the case of side-to-end or side-to-side anastomosis after a hole is created on the vessel, the part of the vessel between the clamp 7 and the open end 3 can be flushed with a biocompatible fluid, such as water or a saline solution, to remove any undesired matter, such as diseased or dead tissue or cells, mineral deposits, plague, thrombus, blood clots, etc., that may be present in the vessel. In one embodiment, the solution is sterile.

Referring now to FIG. 3, the inside of the vessel 1 between the clamp 7 and the end 3 has been filled with the thermoreversible sol-gel 10 which is shown in solid phase by the crossed markings. The area between the clamp 8 and the end 4 is being filled with sol-gel 11 in a liquid phase. In an optional embodiment, the thermoreversible sol-gel 10 can be introduced in its gel phase so as to ease delivery into the vessel. The sol-gel is injected from a suitable delivery apparatus such as a hypodermic needle 9. When the sol-gel material is in the hypodermic needle it may be either in a flowable liquid phase or in a gel phase. In the former case, the composition is delivered in a liquid phase at or below the ambient temperature of the operating field and will undergo a phase transition to a solid gel phase (10) upon the application of heat to raise the temperature to above the transition temperature. In the latter case, the delivery apparatus is kept above the transition temperature of the thermoreversible sol-gel composition which is delivered in a solid gel phase (10) and maintained in that phase by maintaining the temperature at above the transition temperature. It is contemplated that the later is more convenient when the sol-gel composition has a transition temperature of below the temperature of the operating field. If the sol-gel composition has a transition temperature of above the temperature of the operating field, the composition can be preheated and delivered as a gel.

It is contemplated that additional amount of the sol-gel composition may be applied to the lumens during the joining step if needed.

Alternatively, the procedure includes approximating the lumens in a connecting position, such as by partially suturing the two lumens. For example, a few sutures can be applied on the opposite sides of the lumens to bring the lumens in a connecting position. The thermoreversible sol-gel composition can then be applied to the partially sutured opening and form a continuous gel column to fill the lumens to give the structural support for the subsequent procedure that completely joins the lumens. The amount of the sutures applied for this purpose is not intended to fully close the lumens but is to align the lumens so that the gel can be applied to both lumens together, for example, in some embodiment, the sutures are 4-6, or 2-4 and preferably 1-2 sutures on each side. Approximating the lumens can also be preformed by using temporary or permanent anchoring clamps or clips, laser, electrocautery, etc, that are known in the art to connect lumens.

Alternatively, partial suturing can be applied after application of the gel (making sure there is no twists on the lumen) and before application of the glue. For example, the vessels which are deflated due to clamping and lack of blood flow can be inflated with application of a gel. Suture can then be applied to the inflated vessels to partially connect them to bring them in a connecting position before a glue is applied to completely and permanently joining the vessels. The lumens can also be partially ligated by using temporary or permanent anchoring clamps or clips, laser, electrocautery, etc, that are known in the art for connecting lumens.

The thermoreversible sol-gel composition is included in a sufficient amount so as to maintain at least a portion of the distal end of vessel 1 open. In the absence of some force, the side walls of the vessel 1 will contact each other and cause the vessel to close in the absence of flow through the vessel. The solid gel phase (10) imparts sufficient structural rigidity to the lumen to permit the anastomosis to proceed with the vessel in its fully filled form.

As shown in FIG. 4, the two lumens can be joined by applying an adhesive or glue 12 on the two ends of the lumens as well as on the outer surface of the vessel at points 3 and 4 and sealed together. Although FIG. 4 shows the use of a glue, it is to be understood that as described herein, joining or ligation can be accomplished any number of ways, such as suturing or laser soldering or welding. The lumens may also be joined by using electrocautery or other means known in the art.

Sutures are well known in the art as are surgical glues or adhesives and lasers. It is contemplated that the glues used in the methods of this invention are biocompatible and are generally cyanoacrylate-based adhesives, fibrin-based adhesives, polyurethane-based adhesives, polyisocyanate-based adhesives, polyethylene glycol-based glues, latex glues, biologics glues or protein-based glues, and UV curable glues. Suitable glues include but are not limited to the glues described herein. The suture or glue may contain biologically active moieties such as antimicrobial agents (e.g., U.S. Pat. No. 5,762,919).

Laser surgical techniques, such as laser welding or laser soldering, are also known in the art. See, e.g., D. Simhon, in Lasers in Surgery: Advanced Characterization, Therapeutics, and Systems XIV, Vol. 5312, 176-185 (2004); S, Nakata, et al, *The Journal of Thoracic and Cardiovascular Surgery*, 98, 57-62, 1989; and Sanford L. Klein, et al, *Microsurgery*, 15:4, 287-288, 2005. However, laser anastomoses have been reported to cause side effects such as soldering the lumen shut, hemorrhage and degeneration of collagen and protein in the adventitia and media, and under conventional laser anastomosis conditions. See, e.g., S, Nakata, et al, *The Journal of Thoracic and Cardiovascular Surgery*, 98, 57-62, 1989; T. Bavbek, et al, *Opthalmologica* 219, 267-271, 2005. It is contemplated that placing a sol-gel composition inside the lumens will keep the end of the lumen open and protect the tissue from being damaged by the laser beam.

Due to the presence of the gel (in solid phase) significant amounts of adhesive can be used without resulting in vessel closure. In the absence of a structural support provided by the thermoreversible sol-gel 10 within the vessel, the application of pressure to the outside of the vessel, such as the application of the clamps and glue, can cause collapse of the vessel. However, since the thermoreversible sol-gel 10 is holding the vessel open, glue can be applied liberally not only to the ends 3 and 4 which are to be sealed together but the glue 12 can be applied along the surface of the vessel 1 near the point where the seal is to take place. Thus, as shown in FIG. 4, glue has been applied on the outside of the vessel 1 on either side of the point where the ends are sealed. The glue can extend outward in any desired amount. However, with smaller vessels extending the glue out a distance of about 1 mm to about 10 mm is generally sufficient. The glue can extend outward around the entire circumference of the connecting point. After the adhesive 12 has been allowed to cure and seal bonds between the two ends of the vessel, the clamps 7 and 8 can be removed.

In one embodiment the glue also penetrates inward to the surface of the gel thereby providing adherence of the entire tissue cross-section of the first lumen to the second lumen. In another embodiment, the glue is applied not only to the outer surface but also to the cross-sectional surfaces of the lumens to be closed. It is contemplated that the glue may be porous to allow tissue ingrowth and healing across the barrier. For example the glue may contain a porogen which may be an emulsified liquid that is compatible but is immiscible with the glue and can be absorbed by the tissue relatively quickly to leave pores in the glue. It is contemplated that the tissue can infiltrate the glue matrix and heal across as the glue is being reabsorbed by the body. The glue may further comprise a biologically active agent as described herein to facilitate tissue growth, prevent or reduce inflection, restenosis, and other conditions that may be associated with such procedures.

In a still further embodiment, the thermoreversible sol-gel composition, which may have a superior wetting characteristic to the vessel when compared to the glue, may inhibit the glue from penetrating into the inner surface of lumen. In some embodiments, the glue and the sol-gel have limited miscibility. When the vessel is not supported by a sol-gel, connecting two vessels with glue may cause safety concerns due to the possibility that the glue may seal the inside of the lumen. In some embodiments, the glue and the sol-gel are substantially immiscible.

Figure 5:
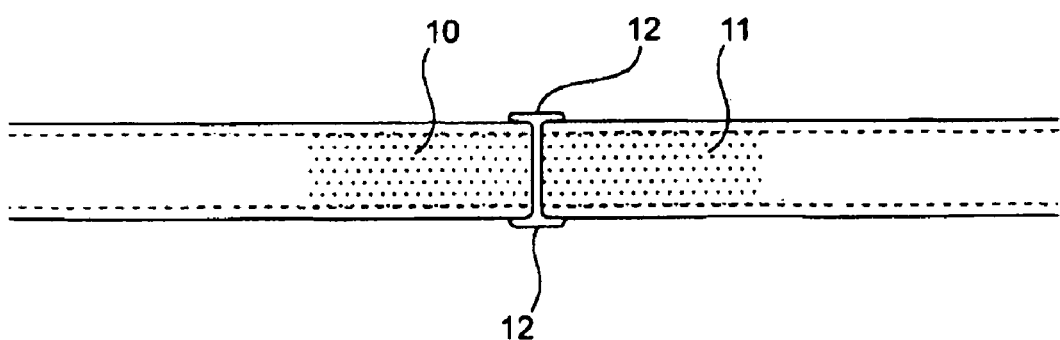
FIG. 5 is a schematic cross-sectional view of the tubular tissue of FIG. 1 with the ends sealed, the sol-gel (reversed to liquid phase) in place and the clamps removed.
Figure 5A:
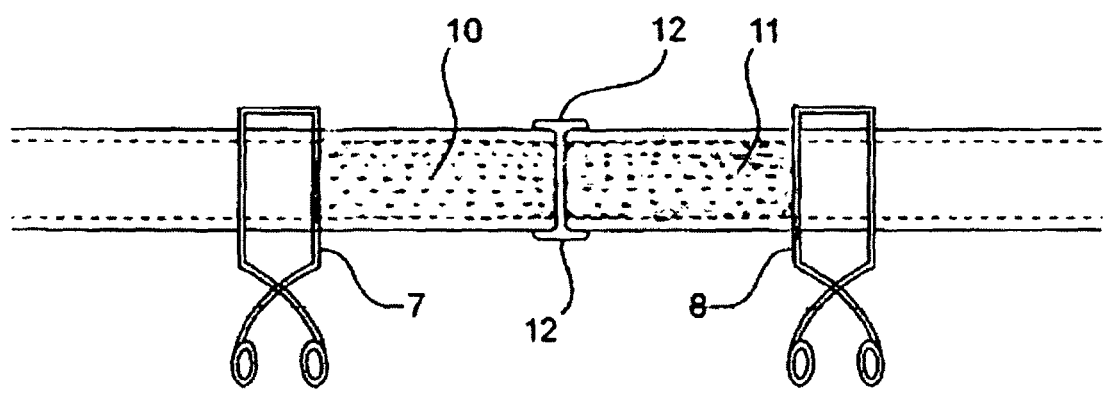
FIG. 5A is a schematic cross-sectional view of the tubular tissue of FIG. 1 with the ends sealed, the sol-gel (reversed to liquid phase) in place and the clamps still present.

In some embodiments, after the lumens are connected and before the clamps are removed, the gel is changed to its liquid state by, for example lowering the temperature of the connected lumens to below the transition temperature of the sol-gel composition by removing the heat source or by applying a cold source, such as cold water or ice, as shown in FIG. 5A. The operating physician then confirms that the phase transition is complete, for example by observing the vessel or by waiting for a sufficient amount of time, to ascertain that no undesired solid mass remains in the vessel which may cause safety concerns. After confirming that all sol-gel has become a liquid, the clamps 7 and 8 are then removed to allow establishment of blood flow and subsequent removal of the liquefied sol-gel by the blood flow. The phase transition can be done before or after the glue is cured or hardened, preferably after the glue is cured or hardened.

When the clamps 7 and 8 are removed (FIG. 5), the heat which was being applied to maintain the composition in a gel state is removed and the gel changes phase to a liquid. Once the gel reverses its phase change to become a liquid and the blood flow causes the sol-gel composition to be dispersed, the vessel reopen as shown in FIG. 6. In other cases, the sol-gel composition can be removed by dissolution in the body fluid, such as blood, that will flow to the site of the sol-gel composition. In still other cases, a combination of phase transition and dissolution can be used. In some embodiments, the temperature-induced phase transition and/or dissolution can be facilitated by other means, such as a change in ionic strength, pH, or light, etc.

Figure 6:
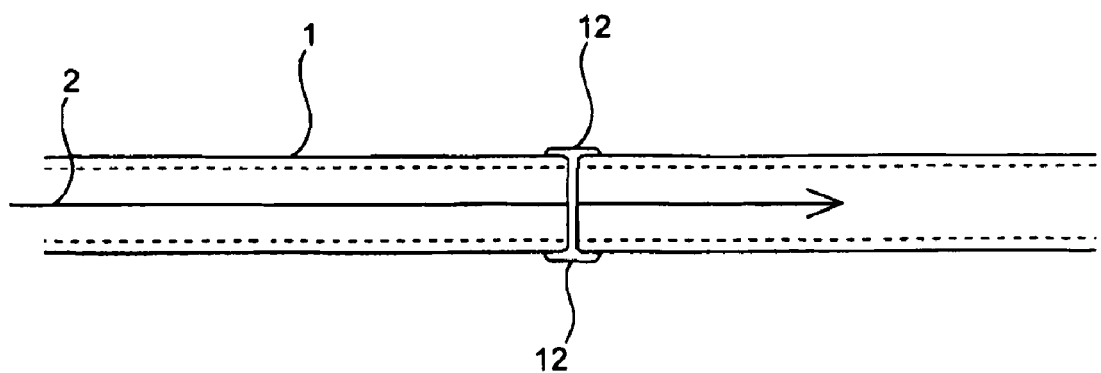
FIG. 6 is a cross-sectional view of the tubular tissue of FIG. 1 showing the sol-gel dissolved and flow restored with the blockage area removed.

At this point as shown in FIG. 5, the glue 12 has cured or hardened. The glue 12 seals the ends of the vessels together but also is applied to the outer surface of the vessel on either side of the point of connection where it is circumferentially applied. Accordingly, when the glue 12 hardens the glue 12 acts as an external stent holding the vessel 1 open after the gel has liquefied. Although it is not necessary to have the glue forming the external stent, this can provide an additional advantage. The glue may be designed so that it remains in place for a considerable period of time or designed so that it dissolves slowly over time as the two ends of the vessel grow together.

It is contemplated that by performing an anastomosis procedure using the compositions and methods of the present invention, the time required to connect the blood vessels can be significantly reduced compared with using conventional hand-sewn anastomosis procedures. This in turn can result in improved outcomes of the procedures in terms of the diameters and patency rates of the vessels connected, anastomotic flow and burst strength, complications caused by the procedures and the mortality rates of the subjects treated.

The methods of this invention can be applies to end-to-end, end-to-side, and side-to-side anastomosis. It can be used to join two or more blood vessels in a patient, or join a blood vessel of the a patient with a lumen selected from the group consisting of arteriovenous graft, arteriovenous shunt, allograft, xenograft, synthetic graft, and cadaver xenograft.

Other aspects of the above method include visualization or imaging of the joining of the lumens and various aspects of procedure as well as monitoring and evaluating the safety and effectiveness of the procedure. In many cases, the procedure is performed under a condition that requires a visual aid in order for the physician to monitor or visualize the progress of the procedure. For example, a magnifying glass is often needed in an anastomosis procedure. In the microvascular context, an operating microscope is often used and a laparoscope is used in a laparoscopic procedure. Other imaging medical instruments may also be employed to monitor the progress and/or the effectiveness of the procedure, including but not limited to collecting blood samples to measure the serum concentration of biomarkers indicative of myocardial performance or the performance of other organs connected to the lumens being conjoined, such as measuring troponin T levels in a coronary artery bypass grafting procedure, measuring the diameters of the conjoined lumens using, for example CT angiography, determining patency and flow through, for example ultrasonic Doppler imaging (e.g., using a visual sonic machine), and/or monitoring the presence of the liquefied sol-gel in the serum or urine. Suitable methods are generally known in the art.

Thus in another aspect, this invention provides methods for imaging the joinder of at least two non-conjoined lumens using the methods of this invention and the stabilization of the geometry of the distal portions of the lumens in a patient.

In some embodiments, the method is a method for imaging the joinder (ligation) of at least two non-conjoined lumens and the stabilization of the geometry of the distal portion of the lumens in a patient, the method comprises:
  (a) acquiring an image of a sol-gel composition of this invention in at least the distal portion of at least one of the lumens;
  (b) acquiring an image showing alignment of the lumens and closure of the aligned lumens to form a conduit.

In some embodiments, the method is a method for imaging the joinder (ligation) of at least two non-conjoined lumens and the stabilization of the geometry of the distal portion of the lumens in a patient, wherein at least one of the lumens is clamped, the method comprises
  (a) acquiring an image of a sol-gel composition of this invention in a gel state in at least the distal portion of at least one of the lumens in proper position to impart structural integrity for the non-conjoined lumens;
  (b) acquiring an image of the proper alignment of the lumens to be joined;
  (c) acquiring an image of the closing of the lumens; and
  (d) acquiring an image of the removal of the clamps.

In some embodiments, the method further comprises acquiring an image of the internal walls of the distal portion of the lumen before and/or after the lumen is flushed with a biocompatible liquid.

In some embodiments, the method is a method for imaging the joining of at least two non-conjoined lumens and the stabilization of the geometry of the distal portions of the lumens in a patient, the method comprises
  (a) acquiring an image of the approximation of the lumens for a connecting position;
  (b) acquiring an image of a biocompatible phase-reversible sol-gel composition of this invention in a gel phase in the distal portion of both lumens in proper position for joining the non-conjoined lumens; and
  (c) acquiring an image of the closure of the lumens to form a conduit.

In some embodiments, the method is a method for imaging the joining at least two non-conjoined lumens and the stabilization of the geometry of the distal portions of the lumens in a patient, wherein at least one of the lumens has a clamp, the method comprises
  (a) acquiring an image of the internal walls of the distal portion of the lumen after the lumen is flushed with a biocompatible liquid;
  (b) acquiring an image of the approximation of the lumens for a connecting position;
  (c) acquiring an image of a biocompatible phase-reversible sol-gel composition in a gel phase in the distal portion of both lumens in proper position for joining the non-conjoined lumens;
  (d) acquiring an image of the closure of the lumens to form a conduit; and
  (e) acquiring an image of the removal of the clamps and establishment of the body fluid.

In another aspect, this invention provides methods for visualizing guidance for the methods of this invention for joining at least two non-conjoined lumens in a patient.

In some embodiments, the method is a method for visualizing guidance for joining at least two non-conjoined lumens and the stabilization of the geometry of the distal portions of the lumens in a patient, the method comprises (a) displaying the provision of a sol-gel composition of this invention in a gel phase in at least the distal portion of at least one of the lumens in proper position to impart structural support for the non-conjoined lumens;
(b) visualizing the proper alignment of the lumens to be joined;
(c) visualizing the closing of the lumens form a conduit; and
(d) visualizing the induction of the phase change of the sol-gel composition in the lumen where the sol-gel changes from the gel phase to a flowable liquid phase.

In some embodiments, the method is a method for visualizing guidance for joining at least two non-conjoined lumens and the stabilization of the geometry of the distal portions of the lumens in a patient, wherein at least one of the lumens has a clamp, the method comprises
(a) displaying the provision of a sol-gel composition of this invention in at least the distal portion of at least one of the lumens in proper position to impart structural support for the non-conjoined lumens;
(b) visualizing the proper alignment of the lumens to be joined;
(c) visualizing the closing of the lumens to form a conduit; and
(e) visualizing the removal of the clamps.

A method for visualizing guidance for joining at least two non-conjoined lumens and the stabilization of the geometry of the distal portions of the lumens in a patient, the method comprises
(a) visualizing the approximation of the lumens for a connecting position;
(b) displaying the provision of a biocompatible phase-reversible sol-gel composition in its gel phase in the distal portion of both lumens in proper position for joining the non-conjoined lumens; and
(c) monitoring by visualization closure of the lumens to form a conduit.

In some embodiments, the method further comprises visualizing the internal walls of the distal portion of the lumen after the lumen is flushed with a biocompatible liquid.

In some embodiments, the method further comprises visualizing the flow of body fluid through the conduit.

A method for visualizing guidance for joining at least two non-conjoined lumens and the stabilization of the geometry of the distal portions of the lumens in a patient, wherein at least one of the lumens has a clamp, the method comprises
(a) visualizing the internal walls of the distal portion of the lumen after the lumen is flushed with a biocompatible liquid;
(b) visualizing the approximation of the lumens for a connecting position;
(c) displaying the provision of a biocompatible phase-reversible sol-gel composition in a gel phase in the distal portion of both lumens in proper position for joining the non-conjoined lumens;
(d) monitoring by visualization closure of the lumens to form a conduit; and
(e) visualizing the flow of body fluid through the conduit.

In another aspect, this invention provides a method for evaluating the effectiveness of the methods of this invention for joining non-conjoined lumens in a patient.

In some embodiments, the method is a method for evaluating the effectiveness of surgical joining of at least two non-conjoined lumens in a patient using a thermoreversible gel, the surgical joining procedure comprising a clamp on at least on one of the lumens to arrest the flow of the fluid therein and the thermoreversible gel in at least the distal portion of at least one of the lumens, alignment of the lumens, closure of the aligned lumens to form a conduit, induction of a phase change of the gel to a flowable liquid, substantial completion of the phase change and removal of the clamp and flowable liquid, the evaluation method comprising
(a) measuring the serum concentration of biomarkers indicative of myocardial performance or the performance of other organs connected to the conjoined lumens; and/or
(b) measuring the diameters of the conjoined lumens, for example using CT angiography; and/or
(c) determining patency and flow, for example through ultrasonic Doppler imaging; and/or
(d) monitoring the presence of the flowable liquid in the serum or urine.

It is contemplated that the compositions and methods of the present invention are useful in other medical procedures, such as reversal of vasectomy, reversal of fallopian tube ligation, and reconstructive tubal surgeries to treat blocked or damaged fallopian tubes. The method can also be used to connect an AV graft or AV shunt or fistula to a blood vessel for hemodialysis as well as below the knee bypass, such as in the treatment of a peripheral arterial disease. Further the compositions and methods of the present invention can be used in alimentary anastomosis. Significant leak rates (about 2-5%) have been resulted by current alimentary anastomosis procedures. Many of the leak incidents are fatal or lead to significant morbidity. Because the alimentary tubes being ligated can be supported inside by the composition of the present invention and the glue can be applied circumferentially outside the point of connection, thus allowing complete sealing, it is contemplated that anastomosis using the compositions and methods of the present invention will significantly reduce the leak rate and lead to decreased mortality and morbidity caused by alimentary anastomosis. The methods and compositions of the present invention can also be used in the treatment of conditions involving urinary tracts, tear ducts, bowel, mammary ducts, pancreatic ducts, bile ducts, and the like.

IV. Kits of The Invention

One aspect of this invention is in the form of a kit of parts. The kit may include specific instructions with respect to how to carry out the methodology of the invention as exemplified above.

Further, the kit may include a container containing the thermoreversible sol-gel composition of the invention, preferably in sterile form, and a delivery device. The delivery device may be a syringe, a pipette, catheter or laparoscopic tool, or the like. Alternatively, the kit may contain a delivery device loaded with the thermoreversible sol-gel composition, again preferably in sterile form. For example, the kit may contain a syringe already loaded with a sterile sol-gel composition or an ampule made from glass or plastic that contains a sterile sol-gel composition, and which has a tip that may be cut open to apply the sol-gel contained therein.

Still further, the kit may include one, two or more clamps of the type which might generally be used in connection with the lumen or type of vessel (or duct, tube, etc.) being treated. Still further, the kit may include sutures, anchoring clamps or clips or surgical glue of the type described above. Still further, the kit may include a heat source to induce a liquid to gel transition and to maintain the sol-gel in its solid or gel like phase until it is to be removed. Such heat source may be a heated air blower capable of delivering warm air, heating pads, a light energy source, an irrigated liquid stream source, an infrared heating apparatus or the like, that can maintain a temperature sufficient to induce the change of phase of the thermoreversible sol-gel. Further, the delivery device may be coupled with a heat or cooling component and serve as a heating or cooling source. The kit may also include a cooling source to induce a gel to liquid transition when it is to be removed. The kit may further include an adhesive delivery system. The kit may further include one or more pharmaceutically active drugs which may be separate from or incorporated into the thermoreversbile sol-gel composition of this invention. Thus, for example, the drug which may be provided separately in the kit or incorporated into the thermoreversible sol-gel composition may include an anticoagulant such as heparin. The thermoreversible sol-gel composition may further include other materials such as a wound healing medicament which aids in healing of the vessel.

Commercially, for ease in practical application, materials may be prepared so that they are sterile and substantially pyrogen free, for example, in accordance with regulatory requirements. Materials and devices may be prepackaged in sterile packaging.

V. EXAMPLES

Example 1

Preparation and Property Determination of a Sol-Gel Composition of this Invention Presented here is a protocol for preparing 100 mL (100 g) of a thermoreversible sol-gel having Formulation 1 listed in Table 1.

Materials:
Phosphate buffered saline ("PBS"): 72 g, pH 7.4, with $Ca^{2+}$ and $Mg^{2+}$;
Poloxamer 407 (BASF Pluronic® F 127): 17 g;
Poloxamer 188 (BASF Pluronic® F 68): 11 g.

Procedure:
The above materials were mixed at 4° C. under high shear to facilitate dispersing the solid poloxamer in the solvent. The heterogenous mixture is then incubated at 4° C. for 12 hours to allow for complete dissolution of the poloxamer in the solvent. The mixture is then further stirred to ensure homogeneity.

Compositions having other formulations can be made similarly according to the total concentration of the poloxamers and the ratios of the two poloxamers.

Water or other aqueous solutions may replace PBS as the solvent. It is preferred that the solvent has an ionic concentration and pH that are close to that of the body fluid so that the resulting thermoreversible sol-gel compositions do not cause substantial damage to surrounding tissues.

To determine the sol-gel transition temperature (the temperature at which the composition transitions from liquid to gel), amounts of each solution were placed between the parallel plates of a stress rheometer (a TA Instruments AR1500EX rheometer was used). The plates were 4 cm in diameter and the gap was set to 1 mm. The elastic modulus was measured using the rheometer at a frequency of 1 Hz and a strain of 1% at different temperatures. Table 1 shows the modulus of several different formulations of the sol-gel composition at various temperatures.

Example 2

An Anastomosis Operation Using a Sol-Gel Composition of this Invention

End to End Anastomosis Surgical Method Performed on Cardiac Tubular Tissues in Rats:

Rats, which are treated and cared for in accordance with all applicable laws and regulations, and in accordance with good laboratory practices, are anesthetized with isoflurane and prepped in sterile fashion with 70% ethanol. The aorta is exposed and isolated with blunt and sharp dissection through a midline laparotomy incision. The aorta is clamped proximally and distally, and subsequently divided and flushed with heparinized saline. In some cases the rat and a sol-gel composition of Formulation 1 are warmed to about 37° C. with sterile water, and then the sol-gel composition of Formulation 1 is injected into severed aortas in a semi-solid state. In other cases the sol-gel composition of Formulation 1 is injected as a liquid and then heated to about 37° C. with a convectional source to solidify it. After direct reapproximation by pushing the ends of the aorta together, the cyanoacrylate adhesive is applied and allowed to cure for 60-120 seconds. The clamps are then removed, and the midline incision is closed in layers with 5-0 vicryl (Ethicon, Inc., Somerset, N.J.) and 4-0 nylon (Ethicon) in a running fashion.

End to Side Anastomosis Surgical Method:

Rats are anesthetized, shaved, and prepped in standard sterile fashion. A midline laparotomy incision is made and the abdominal organs are eviscerated into a moist 4×4 gauze. The iliac bifurcation is isolated with blunt dissection, and the abdominal aorta is clamped proximally and the iliacs are clamped distally. The left iliac is divided just distal to the bifurcation and an arteriotomy is made in the right iliac. The vessels are then flushed with heparinized saline. The abdomen is warmed at the same time a sol-gel composition of Formulation 1 is warmed to a gel (about 37° C.) which is then injected. The left iliac is approximated to the right iliac using the sliding clamps (one clamp is on the proximal aorta and the other is on the distal left iliac). Once the ends are opposed without tension, the cyanoacrylate is applied and allowed to set (~5 min). The clamps are then removed and blood flow is restored.

Example 3

Prophetic Example of Using a Sol-Gel Composition in a Vascular Grafting Procedure In clinical practice, there are some instances where native vessels (i.e. blood vessels of the patient) are not available for bypass grafting or where, especially for older patients, native fistulas require a long maturation time or do not develop sufficiently. In these instances, physicians may choose to use artificial conduits such as grafts comprising polytetrafluoroethylene (PTFE), which can be formed in reinforced or non-reinforced configurations, for example expended PTFE (ePTFE) grafts, manufactured by Gore and others. Synthetic internal arteriouvenous (AV) fistulas or AV grafts, can be placed in many positions in the arms or legs or across the anterior chest wall.

The artificial grafts may be used instead of native vessels in all configurations: end-to-end inter-positional grafting, end-to-side for procedures such as artery to vein shunt for dialysis fistula access, end-to-side bypass procedure both for coronary bypass as well as peripheral bypass. For example, in the below the knee bypass, the graft is attached proximally to the femoral artery and then distally to the popliteal artry and this conduit carries the blood to the distal limb. The procedure for using the graft is similar to the ones for native vessels described above, where the ends of the non-conjoined lumen (expect here one native and one graft) are filled with the gel, followed by alignment of the ends, depositing of glue over the joint, dissolution of the gel is dissolved to complete the anastomosis.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which claimed is:

1. A thermoreversible sol-gel composition for surgical use having a phase transition temperature from a liquid phase to a gel phase of at least 1° C. above or below the temperature of the surgical field and a gel phase elastic modulus of at least 8,000 Pascals, which composition comprises
   a) about 25 to 33% of a mixture of poloxamer 407 and poloxamer 188 in a ratio of between 3:1 and 0.8:1; and
   b) an aqueous salt solution having an ionic strength of from about 0.05 M to about 0.4 M.

2. The composition of claim 1, wherein the transition temperature is at least 3° C. above or below the temperature of the surgical field.

3. The composition of claim 1, which composition is sterile.

4. The composition of claim 1, wherein the phase transition temperature is about 33 to 38° C.

5. The composition of claim 1, wherein the elastic modulus of the gel phase is at least 10,000 Pascals.

6. The composition of claim 1, which composition has a pH of about 6 to 8.

7. The composition of claim 1, comprising about 27 to 29% of a mixture of poloxamer 407 and poloxamer 188 in a ratio of between 1.5:1 and 1.6:1.

8. The composition of claim 1, wherein the salt is selected from the group consisting of sodium chloride, potassium chloride, sodium sulfate, sodium bisulfate, sodium phosphate, monosodium phosphate, disodium phosphate, potassium phosphate, monopotassium phosphate, dipotassium phosphate, calcium chloride, magnesium chloride, and a combination thereof.

9. The composition of claim 1, wherein the aqueous salt solution is phosphate buffered saline.

10. The composition of claim 1, comprising
    about 17% w/w of poloxamer 407;
    about 11% w/w of poloxamer 188;
    and about 72% of phosphate buffered saline solution.

11. The composition of claim 1, further comprises a biologically active agent, a biocompatible dye, or a biocompatible contrasting agent or combinations thereof.

12. The composition of claim 11, wherein the biologically active agent is selected from the group consisting of an anticoagulant, anti-spasm agents, anti-restenosis agents, pro-angiogenic agents, fibroblast growth factor, insulin-like growth factor, vascular endothelial growth factor, hepatocyte growth factor, monocyte chemotactic protein-1, nitroglycerine, everolimus, sirolimus, paclitaxel, rapamycin, biolimus, and combinations thereof, and further wherein the biologically active agent is optionally formulated in sustained release or in gene vectors.

13. The composition of claim 12, wherein the biologically active agent is heparin.

14. A method for joining at least two non-conjoined lumens in a patient which method comprises:
    (a) applying a composition of claim 1 by injection with a hypodermic needle and/or a syringe in at least the distal portion of at least one of the lumens in a manner which imparts structural integrity to said portion of the lumen;
    (b) aligning the lumens;
    (c) joining the aligned lumens to form a conduit; and
    (d) removing the composition thereby establishing body fluid flow through the conduit.

15. The method of claim 14, wherein the lumens are joined by applying a biocompatible adhesive between an end of the first lumen and an end of the second lumen and allowing the adhesive to form bonds between the lumens.

16. The method of claim 15, wherein the biocompatible adhesive is selected from among a cyanoacrylate-based adhesive, a fibrin-based adhesive, a polyurethane-based adhesive, a latex glue, a biologics glue, a polyethylene glycol-based glue, and a polyisocyanate-based adhesive.

17. The method of claim 15, wherein the adhesive is applied to the cross-sectional surfaces of the lumens.

18. The method of claim 15, wherein the adhesive is applied around the circumference of the joined lumens.

19. The method of claim 15, wherein the adhesive further forms an external stent.

20. The method of claim 14, wherein the lumens are joined by a method comprising sutures, electrocautery, or applying laser.

21. The method of claim 14, further comprising an extra step of partially suturing the lumens, where the extra step is performed before and/or after step (a).

22. A method for joining at least two non-conjoined lumens in a patient, wherein at least one of the lumens has a clamp to arrest the flow of the fluid therein, which method comprises:
    (a) providing a thermoreversible sol-gel composition of claim 1 by injection with a hypodermic needle and/or a syringe in a gel phase in at least the distal portion of at least one of the lumens in a manner which imparts structural integrity to said portion of the lumen;
    (b) aligning the lumens;
    (c) closing the aligned lumens to form a conduit;
    (d) inducing a phase transition of the sol-gel wherein the sol-gel changes from the gel phase to a liquid phase;
    (e) confirming substantial completion of the phase transition; and
    (f) removing the clamp(s) thereby establishing flow through the conduit.

23. A method for joining at least two non-conjoined lumens in a patient, which method comprises:
    (a) approximating the lumens in a connecting position;
    (b) providing a thermoreversible sol-gel composition of claim 1 by injection with a hypodermic needle and/or a syringe in a gel phase in the distal portion of both lumens in a manner which imparts structural integrity to said portion of the lumen;
    (c) closing the lumens to form a conduit;
    (d) inducing a phase transition of the sol-gel wherein the sol-gel changes from the gel phase to a liquid phase; and
    (e) establishing flow through the conduit.

24. A method for joining at least two non-conjoined lumens in a patient, wherein at least one of the lumens is clamped to arrest the flow of body fluid therein, which method comprises:
- flushing the distal potion of the clamped lumen with a biocompatible liquid;
- approximating the lumens in a connecting position, which approximating comprises partially suturing the lumens;
- providing a thermoreversible sol-gel composition of claim 1 by injection with a hypodermic needle and/or a syringe in a gel phase in the distal portion of both lumens in a manner which imparts structural integrity to said portion of the lumen;
- closing the lumens to form a conduit with a biocompatible adhesive;
- inducing a phase transition of the sol-gel wherein the sol-gel changes from the gel phase to a liquid phase;
- confirming substantial completion of the phase transition; and
- removing the clamps thereby establishing flow through the conduit and removing the sol-gel composition.

25. The method of claim 14 or 24, wherein a first lumen is a vessel of the cardiovascular system of a human.

26. The method of claim 25, wherein a second lumen is selected from the group consisting of a vessel of the cardiovascular system of a human, an arteriovenous graft, an allograft, a xenograft, cadaver xenograft, a synthetic graft, and an arteriovenous shunt.

27. The method of claim 14 or 24, wherein at least one of the lumens has a diameter of less than 1 mm.

28. The method of claim 14 or 24, wherein the at least two lumens are selected from the group consisting of human fallopian tubes, vas deferens, tubes in the alimentary canal, pancreatic ducts, bile ducts, tear ducts, and mammary ducts.

29. The method of claim 14 or 24, wherein the lumens are joined end to end, end to side or side to side.

30. A kit for connecting at least two non-conjoined lumens within a living mammal, comprising:
- a delivering device; and
- a composition of claim 1.

31. The kit of claim 30, wherein the delivering device is a syringe.

32. The kit of claim 31, wherein the composition is loaded in the syringe.

33. The kit of claim 30, where delivery device is a catheter or a laparoscopic tool.

34. The kit of claim 30, wherein the delivery device is coupled with a heating or cooling component.

35. The kit of claim 30, further comprising at least one clamp for arresting the flow of body fluid in at least one of the non-conjoined lumen, a biocompatible adhesive for sealing the lumens or a heat source.

36. A method for imaging the geometry of the distal portion of at least one lumen being supported by a sol-gel composition of claim 1 and the joinder of the lumen with at least another lumen in a patient, wherein the sol-gel composition is provided to the lumen by injection with a hypodermic needle and/or a syringe.

37. A method for visualizing guidance of the geometry of the distal portion of at least one lumen being supported by a sol-gel composition of claim 1 and the joinder of the lumen with at least another lumen in a patient, wherein the sol-gel composition is provided to the lumen by injection with a hypodermic needle and/or a syringe.

38. A method for evaluating the effectiveness of a method for joining at least two non-conjoined lumens in a patient wherein at least one of the non-conjoined lumens has a sol-gel composition of claim 1 to provide geometry support for the lumen, wherein the sol-gel composition is provided to the lumen by injection with a hypodermic needle and/or a syringe.

* * * * *